(12) United States Patent
Koga et al.

(10) Patent No.: US 7,595,182 B2
(45) Date of Patent: Sep. 29, 2009

(54) ENDOGLUCANASE STCE AND CELLULASE PREPARATION CONTAINING THE SAME

(75) Inventors: Jinichiro Koga, Sakado (JP); Yuko Baba, Sakado (JP); Akitaka Nakane, Sakado (JP); Satoshi Hanamura, Sakado (JP); Tomoko Nishimura, Sakado (JP); Shuichi Gomi, Odawara (JP); Hidetoshi Kubota, Sakado (JP); Toshiaki Kono, Sakado (JP)

(73) Assignee: Meiji Seika Kaisha, Ltd.,, Tokyo (JP)

( * ) Notice: Subject to any disclaimer, the term of this patent is extended or adjusted under 35 U.S.C. 154(b) by 85 days.

(21) Appl. No.: 10/581,717

(22) PCT Filed: Oct. 22, 2004

(86) PCT No.: PCT/JP2004/015733

§ 371 (c)(1),
(2), (4) Date: Jun. 5, 2006

(87) PCT Pub. No.: WO2005/054475

PCT Pub. Date: Jun. 16, 2005

(65) Prior Publication Data

US 2007/0111278 A1    May 17, 2007

(30) Foreign Application Priority Data

Dec. 3, 2003  (JP) ............................. 2003-404020

(51) Int. Cl.
| C12P 21/06 | (2006.01) |
| C12N 9/00 | (2006.01) |
| C12N 9/24 | (2006.01) |
| C12N 1/20 | (2006.01) |
| C12N 1/00 | (2006.01) |
| C12N 15/00 | (2006.01) |
| C07H 21/04 | (2006.01) |

(52) U.S. Cl. ...................... 435/200; 435/69.1; 435/183; 435/252.3; 435/254.4; 435/320.1; 435/484; 536/23.2

(58) Field of Classification Search ................ 435/69.1, 435/183, 200, 252.3, 254.4, 320.1, 484; 536/23.2
See application file for complete search history.

(56) References Cited

U.S. PATENT DOCUMENTS

| 6,001,639 | A | 12/1999 | Schuelein et al. |
| 6,159,720 | A | 12/2000 | Murashima et al. |
| 6,277,596 | B1 | 8/2001 | Watanabe et al. |
| 6,387,690 | B1 | 5/2002 | Schuelein et al. |
| 6,403,362 | B1 | 6/2002 | Moriya et al. |
| 2003/0054539 | A1 | 3/2003 | Schuelein et al. |
| 2003/0092097 | A1 | 5/2003 | Andersen et al. |
| 2007/0099265 | A1 | 5/2007 | Watanabe et al. |

FOREIGN PATENT DOCUMENTS

| EP | 0 112 397 A1 | 7/1984 |
| EP | 0 129 143 A2 | 12/1984 |
| EP | 0 220 016 A2 | 4/1987 |
| EP | 0 307 564 A2 | 3/1989 |
| EP | 0 959 128 A1 | 11/1999 |
| EP | 1 344 820 A1 | 2/2003 |
| EP | 1 291 431 A1 | 3/2003 |
| JP | 11-502701 A | 3/1999 |
| WO | WO 91/17243 A1 | 11/1991 |
| WO | WO 95/02675 A1 | 1/1995 |
| WO | WO 97/30143 A1 | 8/1997 |
| WO | WO 97/43409 | 11/1997 |
| WO | WO 98/03640 A1 | 1/1998 |
| WO | WO 98/03667 A1 | 1/1998 |
| WO | WO 98/08926 A1 | 3/1998 |
| WO | WO 98/11239 A1 | 3/1998 |
| WO | WO 98/12307 | 3/1998 |
| WO | WO 00/24879 A1 | 5/2000 |
| WO | WO 01/90375 A1 | 11/2001 |
| WO | WO 2004/031378 A2 | 4/2004 |
| WO | WO 2005/056787 A1 | 6/2005 |

OTHER PUBLICATIONS

Chica et al. Curr Opin Biotechnol. Aug. 2005;16(4):378-84.*
Seffernick et al. J Bacteriol. Apr. 2001; 183 (8): 2405-10.*
Witkowski et al. Biochemistry. Sep. 7, 1999; 38(36): 11643-50.*
Sen et al. Appl Biochem Biotechnol. Dec. 2007;143(3):212-23.*
Mazuzo Nagayama, "Mechanism of the Action of Detergent Builders in Washing Process", Fragrance Journal, 1995, vol. 11, pp. 33-55.
S.D. Mansfield, et al, "Characterization of Endoglucanases From the Brown Rot Fungi *Gloeophyllum sepiarium* and *Gloeophyllum trabeum*", Enzyme Microbial Technology, vol. 23, 1998, pp. 133-140.
Cindy C. Jenkins, et al, "The Influence of Water Chemsitry on the Enzymatic Degradation of Leaves in Streams", Freshwater Biology, vol. 33, 1995, pp. 245-253.

* cited by examiner

*Primary Examiner*—Christian L Fronda
(74) *Attorney, Agent, or Firm*—Sughrue Mion, PLLC

(57) ABSTRACT

A novel endoglucanase derived from *Staphylotrichum coccosporum*, a polynucleotide encoding the endoglucanase, and a cellulase preparation containing the endoglucanase are disclosed. The endoglucanase or cellulase preparation is available for a washing use or fabric processing, such as a color clarification of a cellulose-containing fabric, a reduction of fuzz, an improvement of the touch feel and appearance of the fabric, providing a localized color change to the fabric, or a reduction of stiffness.

27 Claims, 2 Drawing Sheets

Figure 1

```
NCE4    MRSSPLLRSAVVAALPVLAL---------AADGKSTRYWDCCKPSCGWAK        21
                           ***************  *
STCE1   MRSSPVLRTALAAALPLAALA---------ADGKSTRYWDCCKPSCSWPG        20
                            *  **********  ***
NCE5    MQLPLTTLLTLLPALAA----------AQSGSGRTTRYWDCCKPSCAWPG        23
        Signal peptide→            Catalytic domain→

NCE4    KAPVNQPVFSCNANFQRLTDF-DAKSGCEPGGVAYSCADQTPWAVNDDFA        70
        ** ****** * *****  *      ****  ** ** ********** *
STCE1   KASVNQPVFACSANFQRISDP-NVKSGCD-GGSAYACADQTPWAVNDNFS        68
         *    **  *       *  *   **** **  ** * **  **** *
NCE5    KGPA--PVRTCDRWDNPLFDGGNTRSGCDAGGGAYMCSDQSPWAVSDDLA-       71

NCE4    FGFAATSIAGSNEAGWCCACYELTFTSGPVAGKKMVVQSTSTGGDLGSNH       120
        ****** * *** *** ************** *************** **
STCE1   YGFAATSISGGNEASWCCGCYELTFTSGPVAGKTMVVQSTSTGGDLGTNH       118
        ** **  * * **  *** **************  **       ****** **
NCE5    YGWAAVNIAGSNERQWCCACYELTFTSGPVAGKRMIVQASNTGGDLGNNH       121

NCE4    FDLNIPGGGVGIFDGCTPQFGGLP---GQRYGGISSRNECDRFPDALKPG       167
        ***  *********** ******       * ****  *** ** ** *****
STCE1   FDLAMPGGGVGIFDGCSPQFGGLA---GDRYGGVSSRSQCDSFPAALKPG       165
        **  **********    *  *    *    * ****  *  ** ** ****
NCE5    FDIAMPGGGVGIFNACTDQYGAPPNGWGQRYGGISQRHECDAFPEKLKPG       171
```

Figure 2

```
NCE4    CYWRFDWFKNADNPSFSFRQVQCPAELVARTGCRRNDDGNFPAVQIPSSS           217
        ************* * ******* *****************  **
STCE1   CYWRFDWFKNADNPTFTFRQVQCPSELVARTGCRRNDDGNFPVFTPPSGG           215
        ********  *****        ***  ** * **   ** *
NCE5    CYWRFDWFLNADNPSVNWRQVSCPAEIVAKSGCSR------------------        206
                                                   Linker→

NCE4    TSSPVGQPTSTSTTSTSTTSSPPVQPTTPS-----------GCTAERWA            255
        **      *  *****       * *           ** * ***
STCE1   QSSSSSSSSSAKPTSTSTSTTSTKATSTTSTASSQTSSSTGGGCAAQRWA           265

NCE5    ---------------------------------------------                
                                                   CBD→

NCE4    CQCGGNGWSGCTTCVAGSTCTKINDWYHQCL                              286
        ***** * ******* * ** * ********
STCE1   CQCGGIGFSGCTTCVSGTTCNKQNDWYSQCL                              295

NCE5    -------------------------------
```

ENDOGLUCANASE STCE AND CELLULASE PREPARATION CONTAINING THE SAME

TECHNICAL FIELD

The present invention relates to an endoglucanase STCE and a cellulase preparation containing the same, and a method of treating a cellulose-containing fabric by using the same.

BACKGROUND ART

Conventionally, a cellulose-containing fabric has been treated with cellulase to impart desired properties to the fabric. For example, in the textile industry, treatment with a cellulase is carried out to improve the touch feel and appearance of a cellulose-containing fabric, or to impart a "stonewash" appearance to a colored cellulose-containing fabric, thereby providing the fabric with localized color change [European Patent No. 307,564 (patent reference 1)].

It is known that, when the colored cellulose-containing fabric has been washed repeatedly, a fuzzing of the fabric occurs, which makes the color of the colored fabric unclear. The color of the colored fabric can be clarified by adding cellulase to a detergent to thereby remove the fuzz or to prevent the fuzz formation [European Patent No. 220,016 (patent reference 2), WO95/02675 (patent reference 3), WO97/30143 (patent reference 4), and WO98/08926 (patent reference 5)], and detergents containing cellulase are currently on the market, particularly in Western countries.

As to cellulases which may be contained in a detergent, it is known that, in detergents, a color clarification activity (i.e., an activity to remove fabric fuzz and clarify the color of the fabric) of a purified 43 kD endoglucanase component (EGV) derived from a microorganism belonging to genus *Humicola* was approximately 30 times that of a cellulase preparation containing plural conventional cellulase components [WO91/17243 (patent reference 6)]. Further, it is known that the color of a colored fabric can be clarified by reacting an endoglucanase NCE5 derived from a microorganism belonging to genus *Humicola* (hereinafter sometimes simply referred to as "NCE5") with the colored fabric in a detergent [WO01/90375 (patent reference 7)]. Furthermore, it is known that, in detergents, the color clarification activity of culture liquid obtained by cultivating *Humicola insolens* in which an endoglucanase RCEI derived from a microorganism belonging to genus *Rhizopus* (hereinafter sometimes simply referred to as "RCEI") was overexpressed was more than 20 times that of culture liquid obtained by cultivating *Humicola insolens* in which RCEI was not overexpressed [WO00/24879 (patent reference 8)].

As described above, it is known that various endoglucanases exhibit the color clarification activity, i.e., the activity to clarify the color of colored fabric, but there are few endoglucanases sufficiently exhibiting this activity when contained in detergents now on the Western market. It is considered that the inhibition or reduction of the activity in the detergents is caused by a large amount of anionic surfactants or builders contained in the detergents.

In addition, tap water used for washing in Western countries is generally hard, and contains a large amount of divalent cations, such as $Ca^{2+}$ or $Mg^{2+}$. Because the divalent cations drastically reduce a detergent activity of each surfactant contained in the detergents, the detergents contain one or more builders which adsorb the divalent cations ["Fragrance Journal", 1995, vol. 11, p. 33-55 (non-patent reference 1)]. Further, because the hardness of tap water varies in accordance with countries or regions, the kind and/or the amount of the builders are appropriately selected in accordance with countries or regions. Furthermore, it is known that the divalent cations affect not only the detergent activity of the detergent, but also the cellulase activity [Mansfield, S. D. et al., "Enzyme Microb. Technol." 23, 1998, p. 133-140 (non-patent reference 2), and Jenkins, C. C. AND Suberkropp, K., "Freshwater Biology", vol. 33, No. 2, 1995, p. 245-253 (non-patent reference 3)]. Therefore, according to the hardness of water, a problem in which an inhibition of the cellulase activity reduces the color clarification activity to be desired, or a problem in which an enhancement of the cellulase activity reduces the strength of fabric, occurs.

Because the builder itself affects the cellulase activity, it is difficult to alleviate the effect of the hardness of water on the color clarification activity of the cellulase, by adding thereto the builder. Therefore, a cellulase not easily affected by the hardness of water and exhibiting a stable color clarification activity is desired.

Conventionally, cellulose-containing fabric is treated with a mixture of plural cellulase components, as a cellulose preparation. However, a large amount of cellulase is necessary to obtain a desired effect for the cellulose-containing fabric, and therefore, the development of the cellulose preparation has been retarded by the difficulty caused by this necessity. In many cases, a cellulase preparation is provided as a preparation comprising a large amount of endoglucanase having a high activity. As a process for preparing the cellulase preparation, processes for overexpressing a desired endoglucanase having a high activity in host cells, using genetic recombination techniques, are known [WO91/17243 (patent reference 6), WO98/03667 (patent reference 9), and WO98/11239 (patent reference 10)].

As preferable host cells used in the processes, there may be mentioned, for example, filamentous fungi belonging to Hyphomycetes, such as filamentous fungi belonging to *Aspergillus*, *Humicola*, or *Trichoderma*. As the host for preparing cellulase used in a detergent, the filamentous fungi belonging to *Aspergillus* or *Humicola*, which produce neutral cellulase, is preferable to those belonging to *Trichoderma*, which produce acidic cellulase, because the pH in the detergent is alkaline. Particularly, in view of the industrial production of the enzyme, the filamentous fungi belonging to *Humicola* having a high productivity is most preferable [WO01/90375 (patent reference 7) and WO98/03640 (patent reference 11)].

However, when a filamentous fungus belonging to *Humicola* is used to express a gene derived from a different species (i.e., exogenous gene), the expression is often inhibited because features in the nucleotide sequence of the gene (such as codon usage in the gene) are different. In this case, it is necessary to modify the exogenous gene. For example, when the endoglucanase RCEI derived from a microorganism belonging to genus *Rhizopus* belonging to Zygomycetes is overexpressed in *Humicola insolens*, the gene encoding RCEI should be optimized in accordance with the codon usage of the host cell [WO00/24879 (patent reference 8)]. However, if such an optimization is carried out, it will be difficult to express an exogenous gene as much as endogenous genes. Further, even when the enzyme of interest is expressed and produced in a host, it is anticipated that the enzyme is digested with proteases or the like contained in a culture liquid during cultivation to obtain the enzyme as digested products or partial fragments.

[patent reference 1] European Patent No. 307,564
[patent reference 2] European Patent No. 220,016
[patent reference 3] International Publication WO95/02675
[patent reference 4] International Publication WO97/30143

[patent reference 5] International Publication WO98/08926
[patent reference 6] International Publication WO91/17243
[patent reference 7] International Publication WO01/90375
[patent reference 8] International Publication WO00/24879
[patent reference 9] International Publication WO98/03667
[patent reference 10] International Publication WO98/11239
[patent reference 11] International Publication WO98/03640
[non-patent reference 1] "Fragrance Journal", 1995, vol. 11, p. 33-55
[non-patent reference 2] Mansfield, S. D. et al., "Enzyme Microb. Technol." 23, 1998, p. 133-140
[non-patent reference 3] Jenkins, C. C. AND Suberkropp, K., "Freshwater Biology", vol. 33, No. 2, 1995, p. 245-253

DISCLOSURE OF THE INVENTION

Problems to be Solved by the Invention

For use in washing or in fabric processing, various cellulases were isolated from filamentous fungi belonging to genus *Trichoderma, Rhizopus, Mucor, Phycomyces*, or the like, and genes encoding the cellulases were also isolated. However, a cellulase exhibiting a high color clarification activity in a Western-type detergent containing a large amount of anionic surfactants and builders, not easily affected by the hardness of tap water, and exhibiting a stable color clarification activity has not been reported.

Further, if a cellulase gene which can be overexpressed in an excellent filamentous fungus belonging to genus *Humicola* without genetic modification is found in a different species, the industrial value of the cellulase gene is inestimable. However, such a gene has not been reported.

MEANS FOR SOLVING THE PROBLEMS

The present inventors found novel proteins having a high endoglucanase activity and genes encoding the proteins, from a microorganism belonging to genus *Staphylotrichum*, from which cellulase enzymes or cellulase genes had not been isolated. An object of the present invention is to provide such novel proteins and genes.

The present inventors found that the novel protein of the present invention, which had a high endoglucanase activity and had been isolated from a microorganism belonging to genus *Staphylotrichum*, exhibited an extremely high color clarification activity to colored cellulose-containing fabric in a Western-type detergent. For example, the color clarification activity in the endoglucanase of the present invention derived from *Staphylotrichum coccosporum*, particularly an endoglucanase STCE1 (hereinafter sometimes simply referred to as "STCE1"), was more than 16 times that in an endoglucanase NCE5 (hereinafter sometimes simply referred to as "NCE5") (WO01/90375) and more than 80 times that in an endoglucanase RCEI (WO00/24879), in a typical European detergent. In this connection, it was known that NCE5 and RCEI were cellulases for a detergent exhibiting a color clarification activity.

Surprisingly, the present inventors found that the endoglucanase STCE1 exhibited a stable color clarification activity, regardless of the hardness of the tap water. For example, the color clarification activity in an endoglucanase NCE4 (WO98/03640) or NCE5 (WO01/90375), known to exhibit a high activity of removing fuzz from a cellulose-containing fabric, is increased when the hardness of the tap water is increased. Conversely, the clarification activity in RCEI (WO00/24879) is decreased when the hardness of tap water is increased. However, the endoglucanase STCE1 of the present invention exhibited a stable color clarification activity, regardless of the hardness of the tap water. Such a cellulase, which exhibits a high color clarification activity in a Western-type detergent and exhibits a stable color clarification activity regardless of the hardness of the tap water, has not been reported.

In addition, surprisingly, the present inventors found that when *Humicola insolens*, which is a different species from *Staphylotrichum coccosporum*, was used as a host cell, the endoglucanase STCE1 derived from *Staphylotrichum coccosporum* was overexpressed in the host cell without modifying the endoglucanase STCE1 gene.

The present invention provides a novel protein exhibiting an endoglucanase activity and derived from a microorganism belonging to genus *Staphylotrichum*, a gene encoding the novel protein, and a cellulase preparation containing the protein and exhibiting excellent properties. Further, the present invention provides a host cell transformed with the gene encoding the protein, and a process for producing the protein comprising the steps of cultivating the host cell and collecting the protein. Furthermore, the present invention provides a method for treating a cellulose-containing fabric with the protein of the present invention or the cellulase preparation of the present invention.

The present invention includes the following:
[1] A protein having an endoglucanase activity and derived from a microorganism belonging to genus *Staphylotrichum*.
[2] The protein of [1], having
(A) an encoglucanase activity, and
(B) the amino acid sequence of SEQ ID NO: 1 at the N-terminus thereof.
[3] The protein of [2], having
(A) an encoglucanase activity,
(B) the amino acid sequence of SEQ ID NO: 1 at the N-terminus thereof, and
(C) an average molecular weight of 49 kD, determined by a sodium dodecyl sulfate-polyacrylamide gel electrophoresis.
[4] The protein of [2], having
(A) an encoglucanase activity,
(B) the amino acid sequence of SEQ ID NO: 1 at the N-terminus thereof, and
(C) an average molecular weight of 45 kD, determined by a sodium dodecyl sulfate-polyacrylamide gel electrophoresis.
[5] The protein of any one of [1] to [4], derived from *Staphylotrichum coccosporum*.
[6] A protein selected from the group consisting of:
(a) a protein comprising the amino acid sequence of SEQ ID NO: 3,
(b) a modified protein comprising an amino acid sequence in which one or plural amino acids are deleted, substituted, inserted, or added in the amino acid sequence of SEQ ID NO: 3, and having an endoglucanase activity, and
(c) a homologous protein comprising an amino acid sequence having at least an 85% homology with that of SEQ ID NO: 3, and having an endoglucanase activity.
[7] A polynucleotide encoding the protein of any one of [1] to [6].
[8] A polynucleotide selected from the group consisting of:
(i) a polynucleotide comprising the nucleotide sequence consisting of nucleotides 64-948 of SEQ ID NO: 2,
(ii) a polynucleotide comprising a nucleotide sequence in which one or plural nucleotides are deleted, substituted, inserted, or added in the nucleotide sequence consisting of nucleotides 64-948 of SEQ ID NO: 2, and encoding a protein having an endoglucanase activity, and (iii) a polynucleotide hybridizing under stringent conditions to a polynucleotide consisting of the nucleotide sequence consisting of nucleotides 64-948 of SEQ ID NO: 2, and encoding a protein having an endoglucanase activity.

[9] An expression vector comprising the polynucleotide of [7] or [8].

[10] A host cell transformed with the expression vector of [9].

[11] The host cell of [10], wherein the host is a yeast or a filamentous fungus.

[12] The host cell of [11], wherein the yeast is a microorganism belonging to genus *Saccharomyces, Hansenula*, or *Pichia*.

[13] The host cell of [11], wherein the filamentous fungus is a microorganism belonging to genus *Humicola, Trichoderma, Staphylotrichum, Aspergillus, Fusarium*, or *Acremonium*.

[14] The host cell according of [13], the filamentous fungus is *Humicola insolens* or *Trichoderma viride*.

[15] A process for producing the protein of any one of [1] to [6], comprising the steps of:
cultivating the host cells of any one of [10] to [14], and collecting the protein from the host cells or a culture obtained by the cultivation.

[16] A protein produced by the process of [15].

[17] A cellulase preparation comprising the protein of any one of [1] to [6] and [16].

[18] A detergent composition comprising the protein of any one of [1] to [6] and [16] or the cellulase preparation of [17].

[19] A method of treating a cellulose-containing fabric, comprising the step of bringing the cellulose-containing fabric into contact with the protein of any one of [1] to [6] and [16], the cellulase preparation of [17], or the detergent composition of [18].

[20] A method of reducing fuzzing of a cellulose-containing fabric or reducing a rate of the formation of fuzz, comprising the step of bringing the cellulose-containing fabric into contact with the protein of any one of [1] to [6] and [16], the cellulase preparation of [17], or the detergent composition of [18].

[21] A method of reducing weight to improve the touch feel and appearance of a cellulose-containing fabric, comprising the step of bringing the cellulose-containing fabric into contact with the protein of any one of [1] to [6] and [16], the cellulase preparation of [17], or the detergent composition of [18].

[22] A method of color clarification of a colored cellulose-containing fabric, comprising the step of bringing the colored cellulose-containing fabric into contact with the protein of any one of [1] to [6] and [16], the cellulase preparation of [17], or the detergent composition of [18].

[23] A method of providing a localized color change to a colored cellulose-containing fabric, comprising the step of bringing the colored cellulose-containing fabric into contact with the protein of any one of [1] to [6] and [16], the cellulase preparation of [17], or the detergent composition of [18].

[24] A method of reducing stiffness of a cellulose-containing fabric or reducing a rate of the formation of stiffness, comprising the step of bringing the cellulose-containing fabric into contact with the protein of any one of [1] to [6] and [16], the cellulase preparation of [17], or the detergent composition of [18].

[25] The method of any one of [19] to [24], wherein the treatment of the fabric is carried out by soaking, washing, or rinsing the fabric.

[26] A method of deinking waste paper, comprising the step of treating the waste paper with the protein of any one of to [6] and [16], or the cellulase preparation of [17] together with a deinking agent.

[27] A method of improving a water freeness of paper pulp, comprising the step of treating the paper pulp with the protein of any one of [1] to [6] and [16], or the cellulase preparation of [17].

[28] A method of improving a digestibility of animal feed, comprising the step of treating a cellulose-containing fabric with the protein of any one of [1] to [6] and [16], or the cellulase preparation of [17].

EFFECTS OF THE INVENTION

The protein of the present invention, particularly endoglucanase STCE1, is available for washing or fabric processing, such as color clarification of a cellulose-containing fabric, reduction of fuzz, improvement of the touch feel and appearance of the fabric, providing a localized color change to the fabric, or a reduction of stiffness.

BEST MODE FOR CARRYING OUT THE INVENTION

Protein Having Endoglucanase Activity

The term "endoglucanase" as used herein means an enzyme exhibiting an endoglucanase activity, i.e., endo-1,4-β-glucanase (EC 3.2.1.4), which has an activity of hydrolyzing the β-1,4-glucopyranosyl bond of β-1,4-glucan.

The term "endoglucanase activity" as used herein means a CMCase activity. The term "CMCase activity" as used herein means an activity of hydrolyzing carboxymethylcellulose (CMC; Tokyo Kasei Kogyo Co., Ltd.). When a solution containing a protein (enzyme) to be assayed and CMC is incubated for a predetermined period and the amount of reducing sugar released is measured, the amount of the enzyme producing the reducing sugar corresponding to 1 μmol of glucose per minute is defined as 1 unit of the CMCase activity.

The endoglucanase activity can be measured, for example, by the following procedure. That is, 0.5 mL of a solution containing a protein to be assayed is added to 0.5 mL of a 2% CMC solution dissolved in a 50 mmol/L acetate-sodium acetate buffer (pH6.0), and the mixture is incubated at 50° C. for 30 minutes. A concentration of reducing sugar generated in the reaction mixture is measured by the 3,5-dinitrosalicylic acid method (DNS method). More particularly, after incubation for 30 minutes, 3.0 mL of a DNS reagent is added to 1.0 mL of the reaction mixture, the whole is incubated in a boiling water bath for 5 minutes and diluted with 8.0 mL of distilled water, and the absorbance at 540 nm is measured. A calibration curve is drawn using glucose solutions prepared by stepwise dilution, and an amount of reducing sugar generated in the enzyme reaction mixture is determined as that of converted glucose. The activity is calculated by defining the amount of the enzyme producing the reducing sugar corresponding to 1 μmol of glucose per minute, as 1 unit.

The DNS reagent can be prepared in accordance with the disclosures in references such as Sakuzo Hukui, "Seikagaku Jikken-hou 1, Kangen-Tou no Teiryo-hou (Laboratory Manual for Biological Chemistry, Vol. 1, Assay of Reducing Sugar)", pp. 19-20, Japan Scientific Societies Press, or by the following procedure. To 300 mL of a 4.5% aqueous solution of sodium hydrate, 880 mL of a 1% 3,5-dinitrosalicylic acid solution and 255 g of Rochelle salt are added (Solution A). To 22 mL of a 1.0% aqueous solution of sodium hydrate, 10 g of crystalline phenol is added, and then water is added to dissolve it and adjust the volume to 100 mL (Solution B). Then, 6.9 g of sodium hydrogencarbonate is dissolved in 69 mL of Solution B, and Solution A is poured thereinto. The whole is mixed with stirring to dissolve the Rochelle salt, allowed to stand for 2 days, and then filtrated.

The protein of the present invention may be obtained from filamentous fungi, such as a microorganism belonging to genus *Staphylotrichum*, preferably *Staphylotrichum coccosporum*, more preferably *Staphylotrichum coccosporum* IFO 31817, and a mutant strain derived therefrom may be used.

The N-terminal amino acid sequence of the protein of the present invention is typically that of SEQ ID NO: 1. The N-terminal amino acid sequence may be determined, for example, in accordance with the procedure described in Example 2.

According to the present invention, a protein derived from a microorganism belonging to genus *Staphylotrichum*, and having (A) the endoglucanase activity,
(B) the amino acid sequence of SEQ ID NO: 1 at the N-terminus thereof, and
(C) an average molecular weight of 49 kD determined by SDS-PAGE is provided.

According to the present invention, a protein having (A) the encoglucanase activity,
(B) the amino acid sequence of SEQ ID NO: 1 at the N-terminus thereof, and
(C) an average molecular weight of 45 kD determined by SDS-PAGE is provided.

The average molecular weight determined by SDS-PAGE may be determined in accordance with the procedure described in Example 1.

According to another embodiment of the present invention, a protein comprising the amino acid sequence of SEQ ID NO: 3, and a modified protein or a homologous protein thereof are provided.

As "the protein comprising the amino acid sequence of SEQ ID NO: 3", there may be mentioned, for example, a protein consisting of the amino acid sequence of SEQ ID NO: 3; a protein consisting of an amino acid sequence in which a signal peptide sequence is added to that of SEQ ID NO: 3; or a protein consisting of an amino acid sequence in which one or more appropriate marker sequences are added to the N-terminus and/or the C terminus of that of SEQ ID NO: 3.

As the signal peptide sequence, for example, the amino acid sequence consisting of 21 amino acid residues (SEQ ID NO: 33), which is encoded by the nucleotide sequence from the ATG codon at the 1st to 3rd positions to the codon at the 61st to 63rd positions in that of SEQ ID NO: 2, may be used.

As the marker sequence, a sequence for easily carrying out a confirmation of polypeptide expression, a confirmation of intracellular localization thereof, a purification thereof, or the like may be used. As the sequence, there may be mentioned, for example, a FLAG tag, a hexa-histidine tag, a hemagglutinin tag, or a myc epitope.

The term "modified protein" as used herein means a protein comprising an amino acid sequence in which one or plural amino acids (preferably one or several amino acids) are deleted, substituted, inserted, or added in the amino acid sequence of SEQ ID NO: 3, and having the endoglucanase activity. The number of amino acids to be modified (such as deleted, substituted, inserted, or added) in the amino acid sequence of SEQ ID NO: 3 is preferably 1 to 30, more preferably 1 to 10, most preferably 1 to 6. The amino acid(s) to be modified are not particularly limited, so long as the endoglucanase activity is maintained or improved by the modification. For example, one or more amino acids contained in a catalytic domain, a Linker region, or a cellulose-binding domain, as described below, may be modified.

The modified protein of the present invention includes a protein comprising an amino acid sequence in which one or plural amino acids are conservatively substituted in the amino acid sequence of SEQ ID NO: 3, and having the endoglucanase activity. The term "conservative substitution" as used herein means that one or plural amino acid residues contained in a protein are replaced with different amino acids having similar chemical properties so that the activities of the protein are not substantially changed. As the conservative substitution, there may be mentioned, for example, a substitution of a hydrophobic residue for another hydrophobic residue, or a substitution of a polar residue for another polar residue having the same charge.

Amino acids which have similar chemical properties and can be conservatively substituted with each other are known to those skilled in the art. More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine. As acidic amino acids having a negative charge, there may be mentioned, for example, aspartic acid or glutamic acid.

The term "homologous protein" as used herein means a protein comprising an amino acid sequence having at least 85% (preferably 90% or more, most preferably 95% or more) homology (sequence identity) with a protein comprising the amino acid sequence of SEQ ID NO: 3, and having the endoglucanase activity. The homology as used herein is shown as the value (identity) calculated by FASTA3 [Science, 227, 1435-1441 (1985); Proc. Natl. Acad. Sci. USA, 85, 2444-2448 (1988); http://www.ddbj.nig.ac.jp/E-mail/homology-j.html], a known homology search program, in accordance with default parameters.

As typical embodiments of the protein of the present invention, there may be mentioned, for example, endoglucanase STCE1 or endoglucanase STCE3. Hereinafter the endoglucanases STCE1 and STCE3 are collectively referred to as "endoglucanase STCE".

The endoglucanase STCE of the present invention is an endoglucanase belonging to family 45, as shown in Example 2. As known endoglucanase belonging to family 45, there may be mentioned, for example, endoglucanase NCE4 (WO98/03640) or endoglucanase NCE5 (WO01/90375) derived from genus *Humicola*, or endoglucanase RCEI (WO00/24879) derived from genus *Rhizopus*.

In FIGS. 1 and 2, an alignment of the amino acid sequences of endoglucanase STCE1 [signal peptide (SEQ ID NO: 33) and a mature protein (SEQ ID NO: 3)] of the present invention, known endoglucanase NCE4 [signal peptide (SEQ ID NO: 34) and a mature protein (SEQ ID NO: 35)], and known endoglucanase NCE5 [signal peptide (SEQ ID NO: 36) and a mature protein (SEQ ID NO: 37)] is shown.

FIG. 1 shows the alignment of the former half (i.e., the N-terminal side), and FIG. 2 shows that of the latter half (i.e., the C-terminal side). The symbol "*" in FIGS. 1 and 2 indicates an amino acid consensus to that in STCE1.

As shown in FIGS. 1 and 2, endoglucanases belonging to family 45 contain the catalytic domain (1st to 207th) as a common domain, and sometimes contain the Linker region (208th to 258th) and/or the cellulose-binding domain (CBD) (259th to 295th). In this connection, the numbers in parentheses after the above domains represent the amino acid numbers in the amino acid sequence (SEQ ID NO: 3) of endoglucanase STCE1.

Among each region, there are many conservative amino acids between endoglucanases in the catalytic domain and the cellulose-binding domain, but no remarkable conservative region is observed in the Linker region. Regions containing many conservative amino acids (for example, the catalytic domain or cellulose-binding domain, particularly the catalytic domain), or common amino acids contained in the regions are considered as important regions or amino acids for the enzyme activity of the endoglucanase (such as STCE1) of the present invention. Therefore, when an amino acid modification (for example, deletion, substitution, insertion, and/or addition, particularly conservative substitution) is carried out in a region or amino acid other than such important regions or amino acids, a modified or homologous protein maintaining the enzyme activity can be obtained with a high percentage, without undue experiment.

Further, even if in the regions containing many conservative amino acids, a modification of noncommon amino acid(s) between or among endoglucanases to different amino acid(s) [preferably amino acid(s) which are similar and can be conservatively substituted] may probably maintain the enzyme activity. Therefore, by such a modification, a modified or homologous protein maintaining the enzyme activity can be obtained with a high percentage, without undue experiment.

In this connection, even if common amino acid(s) in the region containing many conservative amino acids are modified to different amino acid(s), the enzyme activity is sometimes maintained. Particularly, in a modification to amino acid(s) which are similar and can be conservatively substituted, the percentage is increased. The modified or homologous protein of the present invention includes a protein in which one or more amino acids contained in any region, such as the catalytic domain, Linker region, or cellulose-binding domain, are modified, so long as it exhibits the endoglucanase activity (that is, an endoglucanase activity before modification is maintained or improved).

The protein of the present invention may be isolated and purified from a microorganism, for example, as described in Example 1. Alternatively, a polynucleotide encoding the protein of the present invention may be expressed in an appropriate host by genetic recombination techniques as described below, and the produced protein may be isolated and purified to obtain the protein of the present invention.

Polynucleotide Encoding Protein having Endoglucanase Activity

According to the present invention, polynucleotides encoding a protein comprising the amino acid sequence of SEQ ID NO: 3, a modified protein thereof, and a homologous protein thereof are provided. When the amino acid sequence of a protein is given, a nucleotide sequence encoding the amino acid sequence can be easily selected, and thus various nucleotide sequences encoding the protein of the present invention can be selected. The term "polynucleotide" as used herein includes DNA and RNA, and DNA is preferable.

Typically, the polynucleotide of the present invention may be selected from the group consisting of:

(i) a polynucleotide comprising the nucleotide sequence of nucleotides 64-948 of SEQ ID NO: 2,
(ii) a polynucleotide comprising a nucleotide sequence in which one or plural nucleotides are deleted, substituted, inserted, or added in the nucleotide sequence consisting of nucleotides 64-948 of SEQ ID NO: 2, and encoding a protein having the endoglucanase activity, and
(iii) a polynucleotide hybridizing under stringent conditions to a polynucleotide consisting of the nucleotide sequence consisting of nucleotides 64-948 of SEQ ID NO: 2, and encoding a protein having the endoglucanase activity.

In the nucleotide sequence consisting of nucleotides 64-948 of SEQ ID NO: 2, the number of nucleotides to be deleted, substituted, inserted, or added is preferably 1 to 30, more preferably 1 to 18, most preferably 1 to 9.

The term "under stringent conditions" as used herein means the conditions controlled so that a probe comprising the nucleotide sequence consisting of nucleotides 64-948 of SEQ ID NO: 2 hybridizes with a polynucleotide encoding a homologous protein, but does not hybridize with the endoglucanase NCE5 gene (WO01/90375).

The "stringent conditions" may be, for example, the following conditions. In accordance with a protocol attached to an ECL direct DNA/RNA labeling and detection system (Amersham), after a polynucleotide to be tested is prehybridized at 42° C. for an hour, a labeled probe having the full length of a nucleotide sequence encoding the amino acid sequence of endoglucanase STCE1 is added, and hybridization is carried out at 42° C. for 15 hours. After the hybridization, a washing treatment with 0.4 (or less) ×SSC (1×SSC; 15 mmol/L sodium citrate, 150 mmol/L sodium chloride) containing 0.4% SDS and 6 mol/L urea at 42° C. for 20 minutes is repeated twice, and a washing treatment with 5×SSC at room temperature for 10 minutes is carried out twice.

The polynucleotide of the present invention includes a naturally-occurring polynucleotide. Further, the whole can be synthesized. Furthermore, the synthesis may be carried out using part of the naturally-occurring polynucleotide. Typically, the polynucleotide of the present invention may be obtained by screening a genomic library derived from *Staphylotrichum coccosporum* in accordance with an ordinary method commonly used in genetic engineering, for example, using an appropriate DNA probe designed on the basis of information of a partial amino acid sequence.

In the present invention, a typical nucleotide sequence encoding the amino acid sequence of endoglucanase STCE1 has the nucleotide sequence consisting of nucleotides 64-948 of SEQ ID NO: 2. The nucleotide sequence of SEQ ID NO: 2 has an open reading frame from the ATG codon at the 1st to 3rd positions to the TAA codon at the 949th to 951st positions. The nucleotide sequence at the 64th to 66th positions corresponds to the N-terminal amino acid of a mature protein of endoglucanase STCE1 consisting of 295 amino acid residues.

Expression Vector and Transformant

According to the present invention, an expression vector comprising a polynucleotide having a nucleotide sequence encoding a protein comprising the amino acid sequence of SEQ ID NO: 3, or a modified protein or homologous protein thereof (hereinafter referred to as the polynucleotide of the present invention) so that the polynucleotide may be replicated and the protein may be expressed in a host microorganism, is provided. The expression vector of the present invention can be constructed on the basis of a self-replicating vector (such as a plasmid), which exists as an extrachromosomal element and can replicate independently of the replication of chromosomes. Alternatively, the expression vector of the present invention may be a vector which is integrated into the genome of the host microorganism and replicated together with chromosomes, when the host is transformed with the vector. The construction of the vector of the present invention can be carried out by ordinary procedures or methods commonly used in genetic engineering.

To express a protein having a desired activity by transforming a host microorganism with the expression vector of the present invention, it is preferable that the expression vector contains, for example, a polynucleotide capable of controlling the expression, or a genetic marker to select transformants, in addition to the polynucleotide of the present invention. As the polynucleotide capable of controlling the expression, for example, a promoter, a terminator, or a polynucleotide encoding a signal peptide for secretion, may be used in the present invention. The promoter which can be used in the present invention is not particularly limited, so long as it shows a transcriptional activity in a host microorganism. The promoter can be obtained as a polynucleotide which controls the expression of a gene encoding a protein the same as or different from that derived from the host microorganism. The signal peptide is not particularly limited, so long as it contributes to the protein secretion in a host microorganism. The signal peptide can be obtained as a polynucleotide derived from a gene encoding a protein same as or different from that derived from the host microorganism. The genetic marker can be appropriately selected in accordance with the method for selecting a transformant. As the genetic marker, for example, a drug resistance gene or a gene complementing an auxotrophic mutation can be used in the present invention.

According to the present invention, a microorganism transformed with the expression vector is provided. A host-vector system which can be used in the present invention is not particularly limited. For example, a system utilizing *E. coli*, Actinomycetes, yeasts, or filamentous fungi, or a system for the expression of a fusion protein using such a microorganism can be used. Transformation of a microorganism with the expression vector can be carried out in accordance with an ordinary method In the present invention, the transformant of the present invention is cultured, and the resulting transformant or culture is used to obtain the protein of the present invention. According to another embodiment of the present invention, the process for producing the novel protein of the present invention can be provided. Cultivation of the transformant (including culturing conditions) can be carried out in a fashion substantially similar to that of the original host used to prepare the transformant. As the method for recovering the protein of interest after the cultivation of the transformant, commonly used procedures can be carried out.

According to a preferable embodiment, a yeast cell capable of expressing endoglucanase encoded by the polynucleotide of the present invention is provided. As the yeast cell, there may be mentioned, for example, a microorganism belonging to genus *Saccharomyces, Hansenula*, or *Pichia*, such as *Saccharomyces cerevisiae*.

As the most preferable process of producing the novel protein of the present invention, a method of expressing the protein in a filamentous fungus belonging to Hyphomycetes is provided. As preferable filamentous fungi which may be used as a host in the present invention, there may be mentioned, for example, filamentous fungi belonging to genus *Humicola, Trichoderma, Staphylotrichum, Aspergillus, Fusarium*, or *Acremonium*, more preferably *Humicola* or *Trichoderma*. More particularly, there may be mentioned, for example, *Humicola insolens, Humicola* thermoidea, *Trichoderma viride, Trichoderma reesei, Trichoderma longibrachiatum, Staphylotrichum coccosporum, Aspergillus niger, Aspergillus oryzae, Fusarium oxysporum*, or *Acremonium cellulolyticus*, preferably *Humicola insolens* or *Trichoderma viride*.

Use of Cellulase/Cellulase Preparation

The present invention relates to a cellulase preparation comprising the protein of the present invention (for example, the protein comprising the amino acid sequence of SEQ ID NO: 3, the modified protein or homologous protein thereof, or a protein obtainable by cultivating the host cell of the present invention).

Conventionally, the cellulase preparation may contain, for example, fillers (for example, lactose, sodium chloride, or sorbitol), antiseptics, and/or nonionic surfactants, in addition to the cellulase enzyme. The form of the cellulase preparation may be solid or liquid, such as powder, particulate, granule, non-dusting granule, or liquid formulation. In addition to the protein of the present invention, the cellulase preparation of the present invention may contain other cellulase enzymes, such as cellobiohydrolase, β-gulucosidase, and/or endoglucanase other than the endoglucanase of the present invention.

The non-dusting granule (preferably a granule not having a dustability), that is one form of cellulase preparation, can be produced according to the common dry granulation method. That is, a powder protein of the present invention is mixed with one or plural substances selected from the group comprising inorganic salts (such as sodium sulfate or sodium chloride) which are neutral and do not have an effect on the endoglucanase activity; minerals (such as bentonite or montmorillonite) which do not have an effect on the endoglunanase activity; and neutral organic substances (such as starch or grinded cellulose). Thereafter, the powders or the finely suspended suspension of one or plural nonionic surfactants are added to the mixture, and then the obtained product is fully mixed or kneaded. Depending on the situation, a synthetic polymer (such as polyethylene glycol) or a natural polymer (such as starch), which binds solids, is optionally added to the mixture and further kneaded. Thereafter, granulation is carried out by extrusion molding, using, for example, a disk pelleter, and the obtained molded material is then converted into a spherical form using a marumerizer followed by drying, so that non-dusting granules can be produced. The amount of one or plural nonionic surfactants is not particularly limited, and is preferably 0.1 to 50% by weight, more preferably 0.1 to 30% by weight, most preferably 1 to 10% by weight of the total weight of the cellulase preparation of the present invention. It is also possible to coat the surface of granules with a polymer or the like to control the permeation of oxygen or water.

Further, the liquid preparation, which is one of the cellulase preparations (preferably a stabilized liquid), can be prepared by blending an endoglucanase stabilizer (such as a synthetic or natural polymer) with a solution containing the protein of the present invention and, if necessary, adding inorganic salts and/or a synthetic preservative. In this case, one or plural nonionic surfactants can be blended with the liquid preparation. The amount of one or plural of the nonionic surfactants is not particularly limited, and is preferably 0.1 to 50% by weight, more preferably 0.1 to 30% by weight, most preferably 1 to 10% by weight of the total amount of the cellulase preparation of the present invention.

Further, the present invention provides a detergent composition comprising the protein of the present invention or the cellulase preparation of the present invention. The detergent composition may also comprise surfactants, which may be anionic, nonionic, cationic, amphoteric, or zwitterionic, or a mixture thereof. The detergent composition may comprise other detergent compositions known in the art, for example, a builder, bleach, bleaching agent, tarnish inhibitor, sequestant, soil releasing polymer, flavor, other enzymes (such as protease, lipase, or amylase), stabilizer for enzyme, granulater, optical brightner, and/or foaming agent. As typical anionic surfactants, there may be mentioned, for example, linear alkyl benzene sulfonate (LAS), alkyl sulphate (AS), α-olefin sulfonate (AOS), polyoxyethylene alkylether sulfonate (AES), α-sulfo fatty acid ester (α-SFMe), or alkali metal salts of naturally-occurring fatty acid. As the nonion surfactants, there may be mentioned, for example, polyoxyethylene alkyl ether (AE), alkylpolyethylene glycol ether, nonylphenol polyethylene glycol ether, fatty acid methyl ester ethoxylate, sucrose, or fatty acid ester of glucose, or esters of alkylglucoside or polyethoxylated alkylglucoside.

The method of the present invention for treating a cellulose-containing fabric is carried out by bringing the cellulose-containing fabric into contact with the protein of the present invention, the cellulase preparation of the present invention, or the detergent composition of the invention. The following properties of cellulose-containing fabric can be improved by the method of the present invention:

(1) Removal of fuzz (reduction of the rate of the formation of fuzz, and reduction of fuzz);
(2) Improvement of the touch feel and appearance of a fabric by reducing weight;
(3) Color clarification of a colored cellulose-containing fabric;
(4) Providing a localized color change to a colored cellulose-containing fabric, that is, providing a stonewash-like appearance and texture to a colored cellulose-containing fabric, typically denim; and
(5) Softening of a fabric (reduction of the rate of stiffness, and a reduction of stiffness).

More particularly, the method of the present invention can be carried out by adding the protein of the present invention, the cellulase preparation of the present invention, or the detergent composition of the present invention into water in which a fabric is or will be soaked, for example, during a soaking, washing, or rinsing of a fabric.

Conditions such as contact temperature or the amount of the protein, the cellulase preparation, or the detergent composition to be added may be appropriately determined in accordance with various other conditions. For example, when reducing the rate of the formation of fuzz or reducing fuzzing of the cellulose-containing fabric, the protein, the cellulase preparation, or the detergent composition in a protein concentration of 0.01 to 20 mg/L is preferably used at a temperature of approximately 10 to 60° C.

When reducing weight to improve the touch feel and appearance of a cellulose-containing fabric, the protein, the cellulase preparation, or the detergent composition in a protein concentration of 0.1 to 50 mg/L is preferably used at a temperature of approximately 10 to 60° C.

When clarifying the color of the colored cellulose-containing fabric, the cellulase, the cellulase preparation, or the detergent composition in a protein concentration of 0.01 to 20 mg/L is preferably used at a temperature of approximately 10 to 60° C.

When providing a localized color change to a colored cellulose-containing fabric, the cellulase, the cellulase preparation, or the detergent composition in a protein concentration of 0.1 to 100 mg/L is preferably used at a temperature of approximately 20 to 60° C.

When reducing the stiffness of a cellulose-containing fabric or reducing the rate of the formation of stiffness, the cellulase, the cellulase preparation, or the detergent composition in a protein concentration of 0.01 to 20 mg/L is preferably used at a temperature of 10 to 60° C.

Further, the present invention relates to a method for deinking waste paper, characterized by using the protein of the present invention or the cellulase preparation of the present invention, in the process of treating the waste paper together with a deinking agent.

The protein or the cellulase preparation of the present invention is useful in the process of producing recycled paper from waste paper, since an efficiency of the deinking can be improved by reacting waste paper therewith. According to the deinking method, the whiteness of waste paper can be remarkably improved by reducing residual-ink fiber.

The deinking agent is not particularly limited, so long as it is agent which can be used in deinking waste paper in general. As the deinking agent, there may be mentioned, for example, alkalis (such as sodium hydroxide or sodium carbonate), sodium silicate, hydrogen peroxide, phosphates, anionic or nonionic surfactants, scavengers such as oleic acid, and assistant agents such as a pH stabilizer, a chelating agent, or a dispersing agent.

Waste paper which can be treated by the deinking method is not particularly limited, so long as it is common waste paper. As the waste paper, there may be mentioned, used newspaper, used magazine paper, and low to middle grade printed used paper which comprises mechanical pulp and chemical pulp; used wood-free paper comprising chemical pulp; or printed waste paper thereof such as coating paper. A paper other than the common waste paper can be treated by the deinking method, so long as it deposits ink.

Further, the present invention relates to a method for improving a water freeness of paper pulp, which comprises the process of treating a paper pulp with the protein of the present invention or the cellulase preparation of the present invention.

According to the method, it is considered that this method can significantly improve a water freeness of paper pulp, without a serious decline of strength. A paper pulp which can be treated by the method is not particularly limited, but there may be mentioned, for example, waste paper pulp, recycled paperboard pulp, kraft pulp, sulfite pulp, thermo-mechanical treatment pulp, and other high-yield pulp.

The present invention relates to a method for improving a digestibility of animal feed, comprising the step of treating the animal feed with the protein of the present invention or the cellulase preparation of the present invention.

According to this method, a digestibility of animal feed can be improved by digesting glucan in animal feed into appropriate molecules having a low molecular weight.

Further, a digestibility of glucan in animal feed can be improved by using the cellulase of the present invention in animal feed. According to the present invention, a method for improving a digestibility of animal feed, comprises the step of treating the animal feed with the protein of the present invention or the cellulase preparation of the present invention.

Deposition of Microorganism

*Staphylotrichum coccosporum* IFO 31817, from which the endoglucanase STCE of the present invention was derived, was domestically deposited in the Institute for Fermentation, Osaka (IFO) in 1985, and the domestic deposit number is IFO 31817. Further, *Staphylotrichum coccosporum* IFO 31817 was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Sep. 28, 2004, and the international deposit number is FERM BP-10135. Furthermore, *Staphylotrichum coccosporum* IFO 31817 was deposited in the Department of Biotechnology, National Institute of Technology and Evaluation (NITE) (Address: 2-5-8 Kazusakamatari, Kisarazu-shi, Chiba 292-0818 Japan), and the deposit number is NBRC 31817. It is clarified by a certificate (dated Nov. 19, 2003) issued by the Department of Biotechnology, NITE that the deposited strain is published and accessible to third parties.

*Escherichia coli* DH5α/pUC118-STCEex of the present invention, i.e., *Escherichia coli* DH5α transformed with plasmid pUC118-STCEex obtained by inserting the STCE1 gene at the BamHI site of plasmid pUC118, was domestically deposited in the International Patent Organism Depositary National Institute of Advanced Industrial Science and Technology on Dec. 1, 2003, and was transferred to an international deposit on Sep. 15, 2004. The international deposit number (a number in parenthesis [ ] following the international deposit number is a domestic deposit number) is FERM BP-10127 [FERM P-19602].

*Humicola insolens* MN200-1, which may be used as a host for the expression vector of the present invention, was domestically deposited in the International Patent Organism Depositary National Institute of Advanced Industrial Science and Technology on Jul. 15, 1996, and was transferred to an international deposit on Jun. 13, 1997. The international deposit number (a number in parenthesis [ ] following the international deposit number is a domestic deposit number) is FERM BP-5977 [FERM P-15736].

*Trichoderma viride* MC300-1, which may be used as a host for the expression vector of the present invention, was domestically deposited in the International Patent Organism Depositary National Institute of Advanced Industrial Science and Technology on Sep. 9, 1996, and was transferred to an international deposit on Aug. 11, 1997. The international deposit number (a number in parenthesis [ ] following the international deposit number is a domestic deposit number) is FERM BP-6047 [FERM P-15842].

EXAMPLES

The present invention now will be further illustrated by, but is by no means limited to, the following Examples.

Example 1

Isolation and Purification of Component Having Absorbent Cotton Fibril-Releasing Activity from *Staphylotrichum coccosporum*

*Staphylotrichum coccosporum* IFO 31817 was cultivated in a (T) medium (2.0% avicel, 2.0% yeast extract, 2.0% corn steep liquor, 1.0% glucose, and 0.2% potassium phosphate) at 28° C. under shaking. After cultivation for 10 days, the mycelia were removed from the culture to obtain a culture supernatant as a crude cellulase preparation solution.

Ammonium sulfate was added to the crude cellulase preparation solution so that a final concentration of ammonium sulfate in the solution became 1.5 mol/L. The solution was applied to a HiTrap™PhenylHP column (Amersham Bioscience) equilibrated with 1.5 mol/L ammonium sulfate solution, and eluted by a stepwise elution method using 1.5 mol/L, 0.9 mol/L, 0.75 mol/L, 0.6 mol/L, 0.15 mol/L, and 0 mol/L ammonium sulfate solutions (in deionized water), to collect fractions. The fractions eluted at concentrations of 0.75 mol/L and 0 mol/L exhibited a high activity of releasing fibril from absorbent cotton.

The fraction eluted at an ammonium sulfate concentration of 0 mol/L was desalted using Ultrafree/Biomax-5K (Millipore), and adjusted to become a 50 mmol/L acetate buffer (pH 4.0). The adjusted fraction was applied to a MonoS 5/5HR column (Amersham Bioscience) equilibrated with a 50 mmol/L acetate buffer (pH 4.0), and eluted by a linear gradient method from a 50 mmol/L acetate buffer (pH 4.0) to a 50 mmol/L acetate buffer (pH 5.0) containing 1 mol/L sodium chloride, to collect fractions. As a result, the fraction eluted at a sodium chloride concentration of approximately 0.05 mol/L exhibited a high activity of releasing fibril from absorbent cotton. The fraction was isolated as STCE1.

The fraction eluted at an ammonium sulfate concentration of 0.75 mol/L was desalted using Ultrafree/Biomax-5K (Millipore), and adjusted to become a 50 mmol/L acetate buffer (pH 4.0). The adjusted fraction was applied to a MonoS 5/5HR column (Amersham Bioscience) equilibrated with a 50 mmol/L acetate buffer (pH 4.0), and eluted by a linear gradient method from a 50 mmol/L acetate buffer (pH 4.0) to a 50 mmol/L acetate buffer (pH 5.0) containing 1 mol/L sodium chloride, to collect fractions. As a result, the fraction eluted at a sodium chloride concentration of approximately 0.05 mol/L exhibited a high activity of releasing fibril from absorbent cotton. The fraction was isolated as STCE3.

The above procedures of fractionation and purification using the columns were repeated many times to obtain purified samples of STCE1 and STCE3 in large quantities.

The STCE1 fraction and the STCE3 fraction were independently detected as a single band in SDS-PAGE, and the average molecular weights (MWs) thereof were approximately 49 kD and approximately 45 kD, respectively. In the SDS-PAGE, Safety Cell Mini STC-808 (Tefco) and Precast Mini Gel 10%-SDS-PAGEmini, 1.0 mm in gel thickness (Tefco) were used, and electorphoresis and staining were carried out in accordance with protocols attached thereto. As molecular markers, Precision Protein Standard (BioRad Laboratories) was used. Both the STCE1 fraction and the STCE3 fraction exhibited a CMCase activity.

The activity of releasing fibril from absorbent cotton was assayed in accordance with a modification of Neena Din et al.'s method [Neena Din et al., "Biotechnology", 9(1991), p. 1096-1099]. That is, an absorbance at 600 nm was measured using a Launder Meter under the following conditions, to determine an amount of fuzz released from absorbent cotton.

Testing machine: Launder Meter L-12 (Daiei Kagaku Seiki MFG., Japan)
Temperature: 40° C.
Time: 120 minutes
Reaction pH: pH 7 (50 mmol/L phosphate buffer)

To a treating solution, an appropriate amount of absorbent cotton and stainless beads were added together with each fraction solution.

Example 2

Sequencing of Partial Amino Acid Sequences of Endoglucanases STCE1 and STCE3 Derived from *Staphylotrichum coccosporum*

(1) Identification of N-terminal Amino Acid Sequences of STCE1 and STCE3

The STCE1 fraction and the STCE3 fraction obtained in Example 1 were subjected to SDS-PAGE, and transferred to a PVDF membrane Problot™ (Applied Biosystems) electrically. The membrane was stained with a CBB staining solution (0.1% Coomassie blue G250, 30% methanol, and 10% acetic acid), and decolorized and air-dried. From the membrane, each portion, on which a protein (STCE1) having a molecular weight of approximately 49 kD corresponding to the STCE1 fraction or a protein (STCE3) having a molecular weight of approximately 45 kD corresponding to the STCE3 fraction was blotted, was excised. Each excised piece was moistened with a minute amount of methanol, washed with lightly a buffer for reduction (8 mol/L guanidine hydrochloride, 0.5 mol/L Tris, 0.3% EDTA-$Na_2$, and 5% acetonitrile), and immersed in a microtube with approximately 100 µL of the buffer for reduction. After 1 mg of dithiothreitol was added to the microtube, the microtube was filled with a nitrogen gas and sealed. The microtube was allowed to stand for more than 1 hour, and 1.5 µL of vinylpyridine (Aldrich) was added thereto, to carry out pyridylethylation of cysteine residues of the protein for more than 20 minutes with occasional stirring, while protected from light. Each piece was washed with de-ionized water followed by 2% acetonitrile, and subjected to a protein sequencer Procise491 (Applied Biosystems) to determine the N-terminal amino acid sequences (25 residues) of STCE1 and STCE3. The N-terminal amino acid sequences (25 residues) of STCE1 and STCE3 accorded with each other, and the sequence was as follows:

N-terminal amino acid sequence of STCE1 and STCE3: Ala-Asp-Gly-Lys-Ser-Thr-Arg-Tyr-Trp-Asp-Cys-Cys-Lys-Pro-Ser-Cys-Ser-Trp-Pro-Gly-Lys-Ala-Ser-Val-Asn (25 residues)(SEQ ID NO: 1)

(2) Identification of Internal Amino Acid Sequences of STCE1 and STCE3

STCE1 and STCE3 obtained in Example 1 were desalted using Ultrafree/Biomax-5K (Millipore), and lyophilized. Each (approximately 40 µg) of STCE1 and STCE3 was independently transferred to a 1.5-mL microtube, and dissolved in 500 µL of the buffer for reduction. After 1.4 mg of dithiothreitol was added to the microtube, the microtube was filled with a nitrogen gas and sealed. The microtube was allowed to stand for 5 hours. Further, 2.7 mg of mono-iodoacetate was added thereto and allowed to stand for 30 minutes while protected from light, to carry out carboxymethylation of cysteine residues of the protein. The whole was desalted and concentrated using Ultrafree/Biomax-5K (Millipore). To each (approximately 10 µg) of reduced carboxymethylated STCE1 and STCE3, an approximately 1/100 mole amount of lysyl endopeptidase (Wako Pure Chemical Industries, Co., Ltd.) was added, and the digestion was carried out in 50 µL of a 50 mmol/L Tris buffer (pH9.0) at 37° C. for 72 hours. When each digested solution of STCE1 and STCE3 was applied to a 173A Micro Blotter System (Applied Biosystems), seven separated peptides were blotted on a PVDF [poly(vinylidene difluoride)] membrane. The amino acid sequences of the obtained peptide fragments were determined using a protein sequencer.

The sequences of internal amino acids of STCE1 were as follows:

(SEQ ID NO: 4)
LE-1: Pro-Ser-Cys-Ser-Trp-Pro-Gly-Lys
(8 residues)

(SEQ ID NO: 5)
LE-2: Ser-Thr-Arg-Tyr-Trp-Asp-Cys-Cys-Lys
(9 residues)

(SEQ ID NO: 6)
LE-3: Asn-Ala-Asp-Asn-Pro-Thr-Phe-Thr-Phe-Arg
(10 residues)

(SEQ ID NO: 7)
LE-4: Ala-Ser-Val-Asn-Gln-Pro-Val-Phe-Ala-Cys
(10 residues)

(SEQ ID NO: 8)
LE-5: Pro-Gly-Cys-Tyr-Trp-Arg-Phe
(7 residues)

(SEQ ID NO: 9)
LE-6: Thr-Met-Val-Val-Gln-Ser-Thr
(7 residues)

(SEQ ID NO: 10)
LE-7: Gln-Asn-Asp-Trp-Tyr-Ser-Gln-Cys-Leu
(9 residues)

When the N-terminal amino acid sequence and the internal amino acid sequences obtained by the peptide mapping were used to carry out a homology search, the result suggested that STCE1 was a novel endoglucanase belonging to family 45.

The sequences of internal amino acids of STCE3 were as follows:

(SEQ ID NO: 11)
LE-8: Pro-Ser-Cys-Ser-Trp-Pro-Gly-Lys
(8 residues)

(SEQ ID NO: 12)
LE-9: Ser-Thr-Arg-Tyr-Trp-Asp-Cys-Cys-Lys
(9 residues)

(SEQ ID NO: 13)
LE-10: Asn-Ala-Asp-Asn-Pro-Thr-Phe-Thr-Phe-Arg
(10 residues)

(SEQ ID NO: 14)
LE-11: Ala-Ser-Val-Asn-Gln-Pro-Val-Phe-Ala-Cys-Ser-Ala-Asn-Phe-Gln-Arg
(16 residues)

(SEQ ID NO: 15)
LE-12: Ser-Gly-Cys-Asp-Gly-Gly-Ser-Ala-Tyr-Ala-Cys-Ala-Asp-Gln-Thr-Pro-Trp-Ala-Val-Asn-Asp-Asn
(22 residues)

(SEQ ID NO: 16)
LE-13: Pro-Gly-Cys-Tyr-Trp-Arg-Phe-Asp-Trp-Phe-Lys
(11 residues)

(SEQ ID NO: 17)
LE-14: Thr-Met-Val-Val-Gln-Ser-Thr-Ser-Thr-Gly-Gly-Asp-Leu-Gly-Thr-Asn
(16 residues)

From a homology search using the N-terminal amino acid sequence and the internal amino acid sequences obtained by the peptide mapping, it was considered that STCE3 was also an endoglucanase belonging to family 45. However, the corresponding internal amino acid sequences of STCE1 and STCE3 were in complete accord with each other, and this suggested that STCE3 was a partially degraded product derived from STCE1.

Example 3

Evaluation of Activity of Purified Endoglucanase STCE1 to Remove Fuzz from Cellulose-Containing Fabric The crude cellulase preparation solution and purified endoglucanase STCE1, obtained in Example 1, were used to evaluate a fuzz-removing activity on a cotton knit fabric.

Cotton knit fabrics stained blue were treated with a surfactant and with rubber balls in a large washer to generate fuzz. The blue cotton knit fabrics with fuzz were treated under the following conditions for removing fuzz, to calculate a protein concentration required to remove approximately 50% of the formed fuzz on the basis of a visual evaluation, in each case of adding the crude cellulase preparation solution or purified endoglucanase STCE1.

Testing machine: Launder Meter L-12 (Daiei Kagaku Seiki MFG., Japan)
Temperature: 40° C.
Time: 60 minutes
Amount of reaction solution: 40 mL
Reaction pH: pH 6 (5 mmol/L phosphate buffer)
To each treating solution, appropriate numbers of rubber balls were added with each endoglucanase solution.

The protein concentration was determined using a Protein Assay Kit (BioRad Laboratories) and bovine serum albumin (as a standard). The result is shown in Table 1.

TABLE 1

| Sample | Protein concentration required to remove 50% of fuzz from cotton fabric (mg/L) |
|---|---|
| Crude cellulase preparation solution | 95.0 |
| Purified STCE1 | 0.21 |

Example 4

Evaluation of Decolorizing Activity of Purified Endoglucanase STCE1 on Indigo-Stained Cellulose-Containing Fabric Using the crude cellulase preparation solution and purified endoglucanase STCE1 obtained in Example 1, a decolorizing treatment of desized 12 oz blue denim was carried out under the following conditions.

Testing machine: 20 kg-washer (Automatic washing machine SCW5101, Sanyo Electric)
Temperature: 55° C.
Time: 60 minutes
Reaction pH: pH 6.2 (6.7 mmol/L phosphate buffer)
Amount of reaction solution: 15 L
To each treating solution, appropriate numbers of rubber balls were added with each endoglucanase solution.

To measure a degree of decolorization, an L value (lightness) of a Lab system was measured using a spectrocolorimeter (CM-525i, Minolta). An increase in the L value (increase in whiteness) to a control (nontreated fabric)(=ΔL value) was determined to evaluate a degree of decolorization. More particularly, ΔL values in ten points were measured (n=10) in each test group, and the average thereof was calculated. A protein concentration required for a ΔL value of 5 was calculated, in each of the cases of adding the crude cellulase preparation solutions and purified endoglucanase STCE1.

The protein concentration was determined using a Protein Assay Kit (BioRad Laboratories) and bovine serum albumin (as a standard). The result is shown in Table 2.

TABLE 2

| Sample | Protein concentration required for ΔL value (decolorization) of 5 (mg/L) |
|---|---|
| Crude cellulase preparation solution | 108.0 |
| Purified STCE1 | 0.37 |

Example 5

Comparative Evaluation of Fuzz-Removing Activity (Color Clarification Activity) of Purified Endoglucanases STCE1, NCE4, NCE5, and RCEI in Detergent Composition Purified endoglucanase STCE1 obtained in Example 1, purified endoglucanase NCE4 obtained from a culture liquid of *Humicola insolens* (WO98/03640), purified endoglucanase NCE5 obtained from a culture liquid of *Humicola insolens* (WO01/90375), and endoglucanase RCEI purified as a single component from *Humicola insolens* in which RCEI was overexpressed [RCEI-H4 (25 kD) in which a cellulose-binding domain was deleted (WO02/42474)] were used, to evaluate a fuzz-removing activity (color clarification activity) on a cotton knit fabric in a Western-type detergent.

Cotton knit fabrics stained blue were treated with a surfactant and with rubber balls in a large washer to generate fuzz. The blue cotton knit fabrics with fuzz were treated in a detergent under the following conditions, to calculate a protein concentration required to remove approximately 50% of the formed fuzz on the basis of a visual evaluation, in each of the cases of adding purified endoglucanases STCE1, NCE4, NCE5, and RCEI.

Testing machine: Launder Meter L-12 (Daiei Kagaku Seiki MFG., Japan)
Temperature: 40° C.
Time: 60 minutes
Amount of reaction solution: 40 mL
Detergent: NEW Persil (Performance Tablets biological) (manufactured by LEVER: obtained in the United Kingdom in March, 2002)
Amount of detergent: 0.8%
Treating solution: hardness-controlled water [25 FH: prepared by diluting hardness-controlled water of 1000 FH containing 80 mmol/L calcium chloride and 20 mmol/L magnesium chloride in deionized water, with deionized water]

To each treating solution, appropriate numbers of rubber balls were added with each endoglucanase solution.

The protein concentration was determined using a Protein Assay Kit (BioRad Laboratories) and bovine serum albumin (as a standard). The result is shown in Table 3.

TABLE 3

| Sample | Protein concentration required to remove 50% of fuzz from cotton fabric (mg/L) |
|---|---|
| Purified STCE1 | 2.5 |
| Purified NCE4 | 2.5 |
| Purified NCE5 | 40.0 |
| Purified RCE1 | 200.0 or more |

Example 6

Effect of Hardness of Tap Water on Fuzz-Removing Activity of Each Purified Endoglucanase Purified endoglucanase STCE1 obtained in Example 1, purified endoglucanase NCE4 obtained from a culture liquid of *Humicola insolens* (WO98/03640), purified endoglucanase NCE5 obtained from a culture liquid of *Humicola insolens* (WO01/90375), and endoglucanase RCEI purified as a single component from *Humicola insolens* in which RCEI was overexpressed [RCEI-H4 (25 kD) in which a cellulose-binding domain was deleted (WO02/42474)] were used, to evaluate a fuzz-removing activity on a cotton knit fabric in hardness-controlled water.

Cotton knit fabrics stained brown were treated with a surfactant and with rubber balls in a large washer to generate fuzz. The brown cotton knit fabrics with fuzz were treated with each purified endoglucanase solution in each hardness-controlled water (0FH, 5FH, 10FH, 20FH, or 40FH) under the following conditions, to calculate a protein concentration required to remove approximately 50% of the formed fuzz on the basis of a visual evaluation, in each of the cases of adding purified endoglucanases STCE1, NCE4, NCE5, and RCEI. The reciprocal of the protein concentration was regarded as the fuzz-removing activity, and a relative value of the fuzz-removing activity in each hardness was determined when the fuzz-removing activity in a hardness of 0FH was regarded as 100.

Testing machine: Launder Meter L-12 (Daiei Kagaku Seiki MFG., Japan)
Temperature: 40° C.
Time: 60 minutes
Amount of reaction solution: 100 mL
Reaction pH: pH 6 (5 mmol/L phosphate buffer)
Treating solution: hardness-controlled water [0 FH, 5 FH, 10 FH, 20 FH, and 40 FH: prepared by diluting hardness-controlled water of 1000 FH containing 80 mmol/L calcium chloride and 20 mmol/L magnesium chloride in deionized water, with deionized water]

To each treating solution, appropriate numbers of rubber balls were added with each endoglucanase solution.

The protein concentration was determined using a Protein Assay Kit (BioRad Laboratories) and bovine serum albumin (as a standard). The result is shown in Table 4.

TABLE 4

| | Relative value of fuzz-removing activity in each hardness (%) | | | | |
|---|---|---|---|---|---|
| | 0FH | 5FH | 10FH | 20FH | 40FH |
| Purified STCE1 | 100 | 100 | 90 | 90 | 90 |
| Purified NCE4 | 100 | 108 | 140 | 160 | 200 |
| Purified NCE5 | 100 | 125 | 150 | 175 | 250 |
| Purified RCE1 | 100 | 70 | 60 | 40 | 25 |

Example 7

Cloning of Endoglucanase STCE Gene

The internal and N-terminal amino acid sequences of STCE1 and STCE3, determined in Example 2, had a homology with that of endoglucanase NCE5 (WO01/90375), belonging to the same family 45 and derived from *Humicola insolens*. To search an endoglucanase STCE gene in the genomic DNA of *Staphylotrichum coccosporum*, a Southern hybridization analysis was carried out using an NCE5 gene as a probe to isolate a homologous gene.

(1) Isolation of Genomic DNA Derived from *Staphylotrichum coccosporum*

*Staphylotrichum coccosporum* IFO 31817 was cultivated in the (T) medium (2.0% avicel, 2.0% yeast extract, 2.0% corn steep liquor, 1.0% glucose, and 0.2% potassium phosphate) at 28° C. for 72 hours, and centrifuged to collect the mycelia. The obtained mycelia was lyophilized, disrupted with a blender, and dissolved in 8 mL of a TE buffer [10 mmol/L Tris-HCl (pH 8.0) and 1 mmol/L EDTA]. To the solution, 4 mL of the TE buffer containing 10% SDS was added, and the mixture was incubated at 60° C. for 30 minutes. After 12 mL of phenol/chloroform/isoamyl alcohol (25:24:1) was further added thereto, the whole was vigorously shaken, and centrifuged. After an aqueous layer was transferred to a new vessel, 1 mL of 5 mol/L potassium acetate was added thereto, and the mixture was allowed to stand on ice for more than 1 hour, and centrifuged. After an aqueous layer was transferred to a new vessel, 2.5 volumes of ethanol were added thereto to precipitate DNAs. The precipitate was dried, and dissolved in 5 mL of the TE buffer. To the solution, 5 μL of a 10 mg/mL RNase A solution was added, and incubated at 37° C. for 1 hour. Further, 50 μL of a 20 mg/mL proteinase K solution was added thereto, and incubated at 37° C. for 1 hour. Then, 3 mL of a polyethylene glycol solution (20% PEG6000 and 2.5 mol/L sodium chloride) was added to precipitate DNAs. After the precipitate was dissolved in 500 μL of the TE buffer, the solution was twice treated with phenol/chloroform/isoamyl alcohol, and precipitated with ethanol. The precipitate was washed with 70% ethanol, dried, and dissolved in an appropriate volume of the TE buffer, to prepare a genomic DNA sample.

(2) Search of NCE5 Homologous Gene by Southern Hybridization

Approximately 10 μg of the genomic DNA, obtained in Example 7(1), of *Staphylotrichum coccosporum* was digested with each restriction enzyme (EcoRI, BamHI, HindIII, XhoI, NcoI, or the like), and subjected to a 0.8% agarose gel electrophoresis. The digested DNAs were transferred to a nylon membrane (Hybond N+ Nyron Transfer Membrane, Amersham). The membrane was treated with 0.4 N sodium hydroxide to immobilize DNAs on the membrane, washed with 5×SSC (75 mmol/L sodium citrate and 750 mmol/L sodium chloride), and dried.

A probe was prepared by digesting a plasmid pJND-c5 (WO01/90375) containing a cDNA of the NCE5 gene with BamHI and collecting a DNA fragment of approximately 700 bp by a 0.8% agarose gel electrophoresis. The probe was labeled using an ECL Direct DNA/RNA labeling detection system (Amersham). In accordance with a protocol attached to the kit, after the membrane on which the genomic DNA was immobilized was prehybridized at 42° C. for 1 hour, the labeled NCE5 probe was added to carry out a hybridization at 42° C. for 15 hours.

After the hybridization, the membrane was washed in accordance with the protocol attached to the kit as follows. The membrane was washed twice with 0.6×SSC (9 mmol/L sodium citrate and 90 mmol/L sodium chloride) supplemented with 0.4% SDS and 6 mol/L urea at 42° C. for 20 minutes, and then washed twice with 5×SSC at room temperature for 5 minutes. After the washed membrane was immersed in a detection solution attached to the kit for 1 minute, a Fuji medical X-ray film (Fuji film) was exposed to the membrane.

As a result, when the genomic DNA was digested with EcoRI, BamHI, XhoI, or NcoI, two bands of different lengths were hybridized with the probe. The result suggested that there were two genes homologous to NCE5 in the genomic DNA of *Staphylotrichum coccosporum*. When the genomic DNA was digested with EcoRI, two bands of approximately 10 kbp and approximately 5 kbp were detected in the hybridization. A gene detected as the band of approximately 10 kbp was cloned in the following procedure.

(3) Preparation of Genomic DNA Library

Genomic DNA of *Staphylotrichum coccosporum* was digested with EcoRI, and subjected to a 0.8% agarose gel electrophoresis using a SeaKemLE agarose (FMC). DNA fragments between approximately 8 to 12 kbp including approximately 10 kbp were extracted and purified in accordance with conventional methods. A phage vector (Lambda DASH II vector; Stratagene) was used to ligate these DNA fragments therewith. The constructs were precipitated with ethanol and dissolved in the TE buffer. The whole amount of the solution and a Gigapack III Gold Packaging kit (Stratagene) were used to package the constructs in the heads of lamda phages, and an *Escherichia coli* XL1-Blue MRA strain was infected with the phages. The obtained phage library (5×10⁴ phages) was used to clone a gene of interest.

(4) Screening of NCE5 Homologous Gene by Plaque Hybridization

The genomic DNA library (EcoRI library) obtained in Example 7(3) was transferred to a nylon membrane (Hybond N+ Nyron Transfer Membrane, Amersham). The membrane was treated with 0.4 N sodium hydroxide to immobilize DNAs on the membrane, washed with 5×SSC, and dried. In accordance with the protocol attached to the above kit, after a prehybridization at 42° C. for 1 hour, the NCE5 probe labeled in Example 7(2) was added to carry out a hybridization at 42° C. for 15 hours.

After the hybridization, the membrane was washed in accordance with the protocol attached to the kit as follows. The membrane was washed twice with 0.6×SSC supplemented with 0.4% SDS and 6 mol/L urea at 42° C. for 20 minutes, and then washed twice with 5×SSC at room temperature for 5 minutes. After the washed membrane was immersed in a detection solution attached to the kit for 1 minute, a Fuji medical X-ray film (Fuji film) was exposed to the membrane. As a result, four phage clones were obtained.

Each of the obtained phage clones was used to infect *Escherichia coli* XL1-Blue MRA therewith. After 18 hours from the infection, phage particles were collected independently. In accordance with a method of Grossberger (Grossberger, D., "Nucleic Acids. Res.", 15, 6737, 1987), the collected phage particles were treated with proteinase K followed by phenol, and precipitated with ethanol, to purify each phage DNA.

(5) Subcloning of NCE5 Homologous Gene

Each of four clones of phage DNAs was digested with plural restriction enzymes, and subjected to a 0.8% agarose gel electrophoresis. The DNAs were transferred to a nylon membrane in accordance with a method of Southern (Southern, E. M., "J. Mol. Biol.", 98, p. 503-517, 1975), and a hybridization was carried out in accordance with the procedure as described in Example 7(4). As a result, common hybridization patterns were obtained in all four clones of phage DNAs, regardless of the kind of restriction enzymes used. When four clones of phage DNAs were digested with SalI, two bands of approximately 4.4 kbp with a strong signal and approximately 2.5 kbp with a weak signal were commonly detected in the hybridization as described in Example 7(4). These results indicated that the homologous gene of interest was located on both DNAs of approximately 4.4 kbp and approximately 2.5 kbp, and therefore, both DNAs were collected and subcloned into plasmid pUC119 at the SalI site thereof, independently. The plasmid obtained by subcloning the DNA of approximately 4.4 kbp was named pSTCE-Sal4.4, and the plasmid obtained by subcloning the DNA of approximately 2.5 kbp was named pSTCE-Sal2.5.

Example 8

Sequencing of Nucleotide Sequence of NCE5 Homologous Gene

The nucleotide sequence of the NCE5 homologous gene, subcloned in Example 7(5), was analyzed as follows.

As a sequencer, A.L.F. DNA sequencer II (Pharmacia Biotech) was used. As a sequencing gel, an acrylamide carrier, available as HydroLink LongRanger (FMC), was used. As various reagents (such as N,N,N',N'-tetramethylethylene diamine, urea, and ammonium persulfate) for gel preparation, A.L.F.-grade reagents (Pharmacia Biotech) were used. The sequencing reaction was carried out using a AutoRead Sequencing Kit (Pharmacia Biotech). Conditions for gel preparation, reaction, and electrophoresis were selected in accordance with protocols attached to these kits.

As described above, the nucleotide sequences of the DNA fragments of approximately 4.4 kbp contained in the plasmid pSTCE-Sal4.4 and approximately 2.5 kbp contained in the plasmid pSTCE-Sal2.5 were determined in accordance with conventional methods. When the determined nucleotide sequences were translated into amino acid sequences, an open reading frame was in complete accord with the N-terminal and internal amino acid sequences of STCE1 shown in Example 2. From the result, it was suggested that the NCE5 homologous gene was a gene encoding STCE1. Hereinafter the NCE5 homologous gene was referred to as "STCE1 gene". It was found, from the amino acid sequence of STCE1 translated from the nucleotide sequence of the genomic DNA, that STCE1 is an endoglucanase belonging to family 45 containing a catalytic domain at the N-terminal side and a cellulose-binding domain at the C-terminal side. Since it was considered that the DNA sequence contained one or more intron regions, a cDNA of the STCE1 gene was isolated by an RT (reverse transcriptase)-PCR in the following procedure.

Example 9

Isolation of cDNA of STCE1 Gene by RT-PCR and Sequencing Thereof (1) Isolation of mRNA from *Staphylotrichum coccosporum*

*Staphylotrichum coccosporum* IFO 31817 was cultivated in 30 mL of the (T) medium (2.0% avicel, 2.0% yeast extract, 2.0% corn steep liquor, 1.0% glucose, and 0.2% potassium phosphate) at 28° C. for 72 hours, and centrifuged to collect the mycelia. The obtained mycelia was lyophilized, and disrupted with a spatula. Total RNAs were isolated using Isogen (Wako Pure Chemical Industries, Co., Ltd.) as described below.

To mycelial powder, 5 mL of Isogen was added. The mixture was stirred for 30 seconds using a vortex mixer, incubated at 50° C. for 10 minutes, and allowed to stand at room temperature for 5 minutes. Then, 0.8 mL of chloroform were added thereto, and the whole was vigorously shaken. After centrifugation, an aqueous layer was transferred to a new vessel. After 2 mL of 4 mol/L lithium chloride was added to the vessel, the whole was mixed, and allowed to stand at −70° C. for 15 minutes. After centrifugation, a supernatant solution was discarded, and a precipitate was dissolved in 1.6 mL of water. To the solution, 1.6 mL of isopropanol was added and mixed, and the mixture was allowed to stand at 4° C. for 30 minutes. After centrifugation, a supernatant solution was discarded, and a precipitate was washed with 75% ethanol, and dissolved in 1.6 mL of water. The solution was precipitated with ethanol, and a precipitate was washed with 75% ethanol, dried, and dissolved in 0.4 mL of water to prepare total RNAs.

Next, mRNAs were prepared using an mRNA isolation kit (Stratagene). To 0.2 mL of the total RNA prepared in Example 9(1), 10 mL of an elution buffer was added, and 5 mL of an oligo-dT solution was added. After a supernatant solution was removed, the oligo-dT was washed three times with a high-salt buffer, washed twice with a low-salt buffer, and eluted with an elution buffer heated at 68° C. The obtained solution was precipitated with ethanol, and a precipitate was washed with 75% ethanol, dried, and dissolved in 15 μL of water to prepare an mRNA fraction.

(2) Isolation of cDNA of STCE1 Gene by RT-PCR

A cDNA of the STCE1 gene was prepared from the mRNAs by an RT-PCR using Takara RNA PCR Kit (AMV) Ver.2.1. A primer sequence for the N-terminal side was determined in view of the N-terminal amino acid sequence of STCE1 and the amino acid sequence translated from the genomic sequence determined in Example 8. A primer sequence for the C-terminal side was determined in view of information of the well-conserved cellulose-binding domain (Hoffren, Annna-Marja. et al., "Protein Engineering", 8, p. 443-450, 1995) and the amino acid sequence translated from the genomic sequence determined in Example 8. The following oligonucleotide primers were prepared, and only cDNA of the STCE1 gene was amplified by a PCR method using, as a template, 1 μL of the mRNAs prepared in Example 9(1).

```
                                          (SEQ ID NO: 18)
STCE1-CN:  5'-GCGGATCCATGCGTTCCTCCCCCGTC-3'
           (26 mer)

(SEQ ID NO: 19)
STCE1-CC:  5'-GCGGATCCTTAAAGGCACTGCGAGTACC-3'
           (28 mer)
```

The RT-PCR reaction was carried out under the following conditions. An RT (reverse transcription) reaction was carried out using a reverse transcriptase in the presence of the primer for the C-terminal side, and then, a PCR for amplification was carried out by adding a Taq polymerase (Recombinant Taq, Takara Shuzo) and the primer for the N-terminal side and repeating a cycle consisting of a reaction at 94° C. for 1 minute, a reaction at 50° C. for 2 minutes, and a reaction at 72° C. for 2 minutes 30 times. The amplified fragment was subjected to an agarose gel electrophoresis to confirm that it was a fragment of approximately 1 kbp. The fragment was subcloned into plasmid pUC18, and the obtained plasmid was named plasmid pUC-STCE1.

(3) Sequencing of STCE1 Gene

The nucleotide sequence of the obtained fragment was determined in accordance with the procedure described in Example 8. The determined nucleotide sequence was compared with that of the genome to determine an intron. As a result, the full length of the nucleotide sequence of the cDNA of the STCE1 gene derived from *Staphylotrichum coccosporum* was determined (SEQ ID NO: 2).

On the basis of the sequence of the cDNA of the STCE1 gene, a DNA fragment containing a coding region of the STCE1 gene including the intron was isolated. A PCR was carried out by using a mixture of four clones of phage DNAs described in Example 7(5) as a template and the following primers STCE-HNBam and STCE-HCBam. The amplified fragment was separated and purified by an agarose gel electrophoresis, and digested with BamHI. The digested fragments were subjected to an agarose gel electrophoresis to separate and purify the fragment of interest.

```
STCE-HNBam:
                                          (SEQ ID NO: 20)
5'-GGG GGA TCC TGG GAC AAG ATG CGT TCC TCC CCC GTC
CTC-3' (39 mer)

STCE-HCBam:
                                          (SEQ ID NO: 21)
5'-GGG GGA TCC GCT CAA AGG CAC TGC GAG TAC CAG TC-
3' (35 mer)
```

The purified fragment of approximately 1.1 kbp was inserted into the BamHI site of plasmid pUC118 to obtain plasmid pUC118-STCEex(FERM P-19602). The nucleotide sequence of the inserted fragment in accordance with the method as described above was determined, to confirm the nucleotide sequence (SEQ ID NO: 22) of the intron and the coding region of the STCE1 gene. In this connection, the stop codon TAA was changed to TGA by using the primer STCE-HCBam in the PCR, but the amino acid sequence of the protein encoded thereby was maintained.

Example 10

Expression of STCE1 gene in *Humicola insolens*

An expression vector pJND-STCE1 for *Humicola insolens* MN200-1 (FERM BP-5977) was constructed, so that 16 amino acid residues at the N-terminus of NCE4 were fused to the remaining amino acid residues of STCE1 in a protein to be expressed, using a plasmid pJND-NCE4 obtained by inserting the NCE4 gene (WO98/03640) into the BamHI site of plasmid pJD01(WO00/24879).

This is because the 16 amino acid residues at the N-terminus of NCE4 accorded with those of STCE1, and thus, the expressed protein in which the 16 amino acid residues at the N-terminus of NCE4 were fused to the remaining amino acid residues of STCE1 was the same as STCE1.

The plasmid pJND-NCE4 was constructed as follows. To insert the NCE4 gene (WO98/03640) into the BamHI site of plasmid pJD01, the following primers containing the BamHI sites at the upstream region adjacent to the initiation codon and at the downstream region adjacent to the stop codon were designed. In accordance with the method described in Example 4(1)1) of WO01/90375, plasmid pCNCE4 (WO98/03640) was used as a template to amplify a DNA fragment with a mutation by a PCR.

```
NCE4-N-BamHI:
                                      (SEQ ID NO: 23)
5'-GGGGATCCTGGGACAAGATGCGTTCCTCCCCTCTCCTCC-3'
(39 mer)

NCE4-C-BamHI:
                                      (SEQ ID NO: 24)
5'-GGGGATCCTGCGTTTACAGGCACTGATGGTACCAGTC-3'
(37 mer)
```

The amplified DNA was digested with BamHI, and subcloned into the BamHI site of plasmid pJD01 [Example D1(2)(b) in WO00/24879] to obtain plasmid pJND-NCE4.

(1) Construction of STCE1-Expression Plasmid

A PCR was carried out using the plasmid pUC-STCE1 prepared in Example 9(2) as a template and the following primers STCE1-N-S9A4 and STCE1-C-FokF. The amplified fragment was separated and purified by an agarose gel electrophoresis, and digested with BamHI and FokI. The digested fragments were subjected to an agarose gel electrophoresis to separate and purify the fragment of interest.

```
STCE1-N-S9A4:
                                      (SEQ ID NO: 25)
5'-GGGATCCTGCGTTTAAAGGCACTGCGAGTACCAG-3'
(34 mer)

STCE1-C-FokF:
                                      (SEQ ID NO: 26)
5'-GGGATGCAAGCCGTCGTGCTCGTG-3'
(24 mer)
```

A PCR was carried out using the plasmid pJND-NCE4 as a template and the following primers STCE1-N-FokR4 and STCE1-C-BamF. The amplified fragment was separated and purified by an agarose gel electrophoresis, and digested with BamHI and FokI. The digested fragments were subjected to an agarose gel electrophoresis to separate and purify the fragment of interest.

```
STCE1-N-FokR4:
                                      (SEQ ID NO: 27)
5'-GGGATGGGCCCAGCCGCACGAAG-3'
(23 mer)

STCE1-C-BamF:
                                      (SEQ ID NO: 28)
5'-GGGATCCTGGGACAAGATGC-3'
(20 mer)
```

The obtained two fragments were inserted into the BamHI site of plasmid pJD01 to obtain plasmid pJND-STCE1. The nucleotide sequence of the inserted fragment was determined in accordance with the method as described above, to confirm that the sequence accorded with that of the STCE1 gene (SEQ ID NO: 2).

(2) Preparation of *Humicola insolens* Transformant with Plasmid pJND-STCE1

*Humicola insolens* MN200-1 was cultivated in an NS medium (3.0% glucose, 2.0% yeast extract, 0.1% peptone, 0.03% calcium chloride, 0.03% magnesium chloride, pH6.8) at 37° C. for 24 hours. The culture was centrifuged at 3000 rpm for 10 minutes to collect mycelia. The obtained mycelia were washed with 0.5 mol/L sucrose, and suspended in 10 mL of an enzyme solution for generating protoplasts (3 mg/mL β-glucuronidase, 1 mg/mL chitinase, 1 mg/mL zymolyase, and 0.5 mol/L sucrose) previously filtrated with a filter (0.45 µm). The suspension was shaken at 30° C. for 60 to 90 minutes to generate protoplasts. The suspension was filtrated, and centrifuged at 2500 rpm for 10 minutes to collect protoplasts. The protoplasts were washed with an SUTC buffer [0.5 mol/L sucrose, 10 mmol/L calcium chloride, and 10 mmol/L Tris-HCl (pH 7.5)].

The protoplasts were suspended in 1 mL of the SUTC buffer. To 100 µL of the suspension, 10 µL of a solution containing 10 µg of plasmid pJND-STCE1 was added, and allowed to stand on ice for 5 minutes. Further, 400 µL of a PEG solution [60% PEG4000, 10 mmol/L calcium chloride, and 10 mmol/L Tris-HCl (pH 7.5)] was added, and allowed to stand on ice for 20 minutes. After 10 mL of the SUTC buffer was added, the whole was centrifuged at 2500 rpm for 10 minutes. The collected protoplasts were suspended in 1 mL of the SUTC buffer, centrifuged at 4000 rpm for 5 minutes, and finally suspended in 100 µL of the SUTC buffer.

The protoplasts treated as above were overlaid, with YMG soft agar, on a YMG medium [1% glucose, 0.4% yeast extract, 0.2% malt extract, and 1% agar (pH 6.8)] containing hygromycin (200 µg/mL), and incubated at 37° C. for 5 days to obtain transformants as colonies.

(3) Cultivation and Identification of Transformant with pJND-STCE1

(i) Evaluation by SDS-PAGE

From the transformants obtained by transforming *Humicola insolens* MN200-1 with plasmid pJND-STCE1 as above, 40 strains resistant to hygromycin were selected. Each strain was cultivated in an (N) medium (5.0% avicel, 2.0% yeast extract, 0.1% polypeptone, 0.03% magnesium sulfate, pH6.8) at 37° C. for 4 days. Each culture supernatant was analyzed by SDS-PAGE [Precast Mini Gel 14%-SDS-PAGEmini, 1.0 mm in gel thickness (Tefco)]. As a result, it was confirmed that a protein having a molecular weight of approximately 45 to 49 kD, which was considered as STCE1, was remarkably overexpressed in 13 clones.

(ii) Identification of N-terminal Amino Acid Residue of Recombinant STCE1

To confirm that the overexpressed protein described in Example 10(3)(i) was derived from the STCE1 gene, the N-terminal amino acid sequence was determined. The culture supernatant was subjected to SDS-PAGE, and separated proteins were electrically transferred to a PVDF membrane in accordance with the procedure described in Example 2. The protein having a molecular weight of approximately 45 to 49 kD was subjected to a protein sequencer. As a result, the determined sequence accorded with the N-terminal amino acid sequence (SEQ ID NO: 1) of endoglucanase STCE1.

Example 11

Evaluation of Activity of STCE1 Expressed in *Humicola insolens* to Remove Fuzz from Cellulose-Containing Fabric Among 13 strains in which the expression of the protein having a molecular weight of approximately 45 to 49 kD was confirmed by SDS-PAGE in Example 10(3), a strain (4A-9) showing a remarkable expression was selected. A culture supernatant of the strain 4A-9 was used to measure a fuzz-removing activity on a cotton knit fabric. As a control, a culture supernatant of the parent strain (i.e., nontransformant) was used. Evaluation was carried out in accordance with the procedure described in Example 3. The blue cotton knit fabrics with fuzz were treated under the above conditions (pH 6, 40° C., 1 hour) with each culture supernatant, to calculate a protein concentration required to remove approximately 100% of the formed fuzz on the basis of a visual evaluation.

The protein concentration was determined using a Protein Assay Kit (BioRad Laboratories) and bovine serum albumin (as a standard). The result is shown in Table 5.

TABLE 5

| | Protein concentration required to remove 100% of fuzz from cotton fabric (mg/L) |
|---|---|
| *Humicola insolens* MN200-1 (parent strain) | 96.3 |
| *Humicola insolens* 4A-9 | 3.5 |

Example 12

Evaluation of Decolorizing Activity of Endoglucanase STCE1 Expressed in *Humicola insolens* on Indigo-Stained Cellulose-Containing Fabric Using Culture supernatants of the STCE1-overexpressed strain (4A-9) obtained in Example 10 and the parent strain (MN200-1) as a nontransformant, a decolorizing treatment of desized 12 oz blue denim was carried out under the following conditions.

Testing machine: 20 kg-washer (Automatic washing machine SCW5101, Sanyo Electric)
Temperature: 55° C.
Time: 60 minutes
Reaction pH: pH 6.2 (6.7 mmol/L phosphate buffer)
Amount of reaction solution: 15 L To each treating solution, appropriate numbers of rubber balls were added with each endoglucanase solution.

With respect to a degree of decolorization, an L value (lightness) in a Lab system was measured using a spectrocolorimeter (CM-525i, Minolta). An increase in the L value (increase in whiteness) to a control (nontreated fabric)(=ΔL value) was determined to evaluate a degree of decolorization. More particularly, ΔL values in ten points were measured (n=10) in each test group, and the average thereof was calculated. A protein concentration required for a ΔL value of 7 was calculated.

The protein concentration was determined using a Protein Assay Kit (BioRad Laboratories) and bovine serum albumin (as a standard). The result is shown in Table 6.

TABLE 6

| | Protein concentration required for ΔL value (decolorization) of 7 (mg/L) |
|---|---|
| *Humicola insolens* MN200-1 (parent strain) | 58.9 |
| *Humicola insolens* 4A-9 | 3.3 |

Example 13

Evaluation of Fuzz-Removing Activity (Color Clarification Activity) of STCE1 Expressed in *Humicola insolens* in Detergent Composition Culture supernatants of the STCE1-overexpressed strain (4A-9) obtained in Example 10 and the parent strain (MN200-1) as a nontransformant were used to evaluate a fuzz-removing activity (color clarification activity) in a Western-type detergent with respect to a cotton knit fabric.

Cotton knit fabrics stained brown were treated with a surfactant and with rubber balls in a large washer to generate fuzz. The brown cotton knit fabrics with fuzz were treated in a detergent under the following conditions, to calculate a protein concentration required to remove approximately 50% of the formed fuzz on the basis of a visual evaluation.

Testing machine: Launder Meter L-12 (Daiei Kagaku Seiki MFG., Japan)
Temperature: 40° C.
Time: 60 minutes
Amount of reaction solution: 40 mL
Detergent: NEW Persil (Performance Tablets biological) (manufactured by LEVER: obtained in the United Kingdom in March, 2002)
Amount of detergent: 0.4%
Treating solution: hardness controlled water [25 FH: prepared by diluting hardness controlled water of 1000 FH containing 80 mmol/L calcium chloride and 20 mmol/L magnesium chloride in deionized water, with deionized water]

To each treating solution, appropriate numbers of rubber balls were added with each culture supernatant.

The protein concentration was determined using a Protein Assay Kit (BioRad Laboratories) and bovine serum albumin (as a standard). The result is shown in Table 7.

TABLE 7

| | Protein concentration required to remove 50% of fuzz from cotton fabric (mg/L) |
|---|---|
| *Humicola insolens* MN200-1 (parent strain) | 833 |
| *Humicola insolens* 4A-9 | 22 |

Example 14

Effect of Hardness in Tap Water on Fuzz-Removing Activity of Each Endoglucanase Expressed in *Humicola insolens*

Culture supernatants of four strains, i.e., the STCE1-overexpressed strain (4A-9) obtained in Example 10, an NCE5-over expressed *Humicola insolens* transformant (WO01/90375), an NCE4-over expressed *Humicola insolens* transformant (WO98/03640), and an RCEI [RCEI-H4 (25 kD) in which a cellulose-binding domain was deleted] overexpressed *Humicola insolens* transformant (WO02/42474), were used to evaluate a fuzz-removing activity in a detergent with respect to a cotton knit fabric, in water having different hardnesses.

Cotton knit fabrics stained brown were treated with a surfactant and with rubber balls in a large washer to generate fuzz. The brown cotton knit fabrics with fuzz were treated with each of four culture supernatants in each hardness controlled water (0FH, 5FH, 10FH, 20FH, or 40FH) under the following conditions.

Testing machine: Launder Meter L-12 (Daiei Kagaku Seiki MFG., Japan)

Temperature: 40° C.

Time: 60 minutes

Amount of reaction solution: 100 mL

Detergent: NEW Persil (Performance Tablets biological) (manufactured by LEVER: obtained in the United Kingdom in March, 2002)

Amount of detergent: 0.4%

Treating solution: hardness controlled water [0 FH, 5 FH, 10 FH, 20 FH, and 40 FH: prepared by diluting hardness controlled water of 1000 FH containing 80 mmol/L calcium chloride and 20 mmol/L magnesium chloride in deionized water, with deionized water]

To each treating solution, appropriate numbers of rubber balls were added with each culture supernatant.

After the treatment, a protein concentration required to remove approximately 50% of the formed fuzz on the basis of a visual evaluation was calculated, and the reciprocal of the protein concentration was regarded as the fuzz-removing activity. Further, a relative value of the fuzz-removing activity in each hardness was determined when the fuzz-removing activity in a hardness of 0FH was regarded as 100. The result is shown in Table 8.

TABLE 8

| | Relative value of fuzz-removing activity in each hardness (%) | | | | |
|---|---|---|---|---|---|
| | 0FH | 5FH | 10FH | 20FH | 40FH |
| a | 100 | 100 | 100 | 100 | 93 |
| b | 100 | 107 | 127 | 140 | 160 |
| c | 100 | 129 | 143 | 171 | 257 |
| d | 100 | 70 | 55 | 40 | 30 |

[a: STCE1-overexpressed *H. insolens*,
b: NCE4-overexpressed *H. insolens*,
c: NCE5-overexpressed *H. insolens*, and
d: RCE1-overexpressed *H. insolens*]

Example 15

Expression of STCE1 Gene in *Trichoderma viride*

(1) Construction of STCE1-Expression Plasmid STCE1N-pCB1

The following primers for mutagenesis, containing the SmaI recognition site at the upstream of the initiation codon and the XhoI recognition site at the downstream of the stop codon, were designed, and the STCE1 gene was amplified by a PCR method as follows.

STCE1-N-SmaI:
(SEQ ID NO: 29)
5'-CAGCCCGGGGCGCATCATGCGTTCCTCCCCTCTCC-3'
(35 mer)

STCE1-C-XhoI:
(SEQ ID NO: 30)
5'-GCCTCGAGTACCTTAAAGGCACTGCGAGTACCA-3'
(33 mer)

The PCR was carried out using plasmid pJND-STCE1 as a template, two synthetic DNAs STCE1-N-SmaI and STCE1-C-XhoI as primers, and a TaKaRa LA Taq with GC buffer (Takara Shuzo), under the conditions as described in a protocol attached to the Taq polymerase. After the reaction, the sample was subjected to an agarose gel electrophoresis, and the separated DNA fragment was digested with SmaI and XhoI to obtain a gene fragment STCE1-N of approximately 0.9 kbp.

Plasmid pCB1-M2 (WO98/11239) was digested with StuI and XhoI to collect a fragment of 7.3 kbp. This fragment of 7.3 kbp was ligated with the gene fragment STCE1-N of approximately 0.9 kbp, using a TaKaRa DNA Ligation Kit Ver.1 (Takara Shozo), to obtain plasmid STCE1N-M2.

Into the XbaI site of the plasmid STCE1N-M2, a hygromycin B-resistant gene cassette derived from PDH25 (Cullen, D., Leong, S. A., Wilson, L. J. AND Henner, D. J., "Gene", 57, p. 21-26, 1987) was inserted to obtain plasmid STCE1N-pCB1. The reaction conditions, such as enzyme reactions, were selected in accordance with protocols attached to the kits. The plasmid STCE1N-pCB1 was constructed to express the STCE1 protein in *Trichoderma* as a host using the initiation codon of STCE1.

(2) Construction of Fusion STCE1-Expression Plasmid STCE1M-pCB1

The following primers for mutagenesis, containing the SphI recognition site at the upstream region adjacent to the codon encoding the N-terminal amino acid (Ala) and the XhoI recognition site at the downstream of the stop codon, were designed, and the STCE1 gene was amplified by a PCR method as follows.

STCE1-M-SphI:
(SEQ ID NO: 31)
5'-CCGCATGCGCTGATCGCAAGTCCACC-3'
(26 mer)

STCE1-C-XhoI:
(SEQ ID NO: 32)
5'-GCCTCGAGTACCTTAAAGGCACTGCGAGTACCA-3'
(33 mer)

The PCR was carried out using plasmid pJND-STCE1 as a template, two synthetic DNAs STCE1-M-SphI and STCE1-C-XhoI as primers, and a TaKaRa LA Taq with GC buffer (Takara Shuzo), under the conditions as described in a protocol attached to the Taq polymerase. After the reaction, the sample was subjected to an agarose gel electrophoresis, and the separated DNA fragment was digested with SphI and XhoI to obtain a gene fragment STCE1-M of approximately 0.9 kbp.

Plasmid pCB1-M2 (WO98/11239) was digested with SphI and XhoI to collect a fragment of 7.3 kbp. This fragment of 7.3 kbp was ligated with the gene fragment STCE1-M of approximately 0.9 kbp, using a TaKaRa DNA Ligation Kit Ver.1 (Takara Shozo), to obtain plasmid STCE1-M2.

Into the XbaI site of the plasmid STCE1-M2, a hygromycin B-resistant gene cassette derived from PDH25 (Cullen, D., Leong, S. A., Wilson, L. J. AND Henner, D. J., "Gene", 57, p. 21-26, 1987) was inserted to obtain plasmid STCE1M-pCB1. The reaction conditions, such as enzyme reactions, were selected in accordance with protocols attached to the kits. The plasmid STCE1M-pCB1 was constructed to express a fusion protein of the STCE1 protein and a pre-pro sequence derived from a CBHI protein in *Trichoderma* as a host using the initiation codon derived from the vector.

(3) Preparation of *Trichoderma viride* Transformants with Plasmids STCE1N-pCB1 and STCE1M-pCB1

*Trichoderma viride* MC300-1 (FERM BP-6047) was cultivated in an S medium (3.0% glucose, 1.0% yeast extract, 0.1% polypeptone, 0.14% ammonium sulfate, 0.2% potassium phosphate, 0.03% magnesium sulfate, pH6.8) at 28° C. for 24 hours, and centrifuged at 3000 rpm for 10 minutes to collect mycelia. The obtained mycelia were washed with 0.5 mol/L sucrose, and suspended in an enzyme solution for generating protoplasts (5 mg/mL novozyme 234, 5 mg/mL cellulase Onozuka R-10, and 0.5 mol/L sucrose) previously filtrated with a filter (0.45 μm). The suspension was shaken at 30° C. for 60 to 90 minutes to generate protoplasts. The suspension was filtrated, and centrifuged at 2500 rpm for 10 minutes to collect protoplasts. The protoplasts were washed with the SUTC buffer as described above.

The protoplasts were suspended in 1 mL of the SUTC buffer. To 100 μL of the suspension, 10 μL of each DNA solution containing 10 μg of plasmid STCE1N-pCB1 or STCE1M-pCB1 was added, and allowed to stand on ice for 5 minutes. Further, 400 μL of a PEG solution [60% PEG4000, 10 mmol/L calcium chloride, and 10 mmol/L Tris-HCl (pH 7.5)] was added, and allowed to stand on ice for 20 minutes. After 10 mL of the SUTC buffer was added, the whole was centrifuged at 2500 rpm for 10 minutes. The collected protoplasts were suspended in 1 mL of the SUTC buffer, centrifuged at 4000 rpm for 5 minutes, and finally suspended in 100 μL of the SUTC buffer.

The protoplasts treated as above were overlaid, with potato dextrose (PD) soft agar (1.3% potato dextrose agar and 17.1% sucrose), on a PD agar medium (3.9% potato dextrose agar and 17.1% sucrose) containing hygromycin B (20 μg/mL), and incubated at 28° C. for 5 days to obtain transformants as colonies.

Example 16

Identification of STCE1 in Culture of *Trichoderma viride* Transformant with STCE1 Gene and Evaluation of Fuzz-Removing Activity (1) Evaluation by HPLC From the transformants obtained by transforming *Trichoderma viride* MC300-1 with plasmid STCE1N-pCB1 or STCE1M-pCB1 as above, 50 strains resistant to hygromycin B were selected. Each strain was cultivated in the S medium at 37° C. for 5 days. Each culture supernatant was analyzed by an HPLC analysis using a TSKgel TMS-250 column (4.6 mm I.D.×7.5 cm) (TOSOH Corporation). In the HPLC analysis, elution was carried out at a flow rate of 1.0 mL/min using a linear gradient of 0% to 80% acetonitrile in 0.05% TFA (trifluoroacetic acid), and peaks were detected at UV 280 nm. As a result, a peak, which was not detected in the culture supernatant of *Trichoderma viride* MC300-1 (wild type), was detected in those of 3 clones of STCE1N-pCB1 transformants and 3 clones of STCE1M-pCB1 transformants. The peak was collected and the N-terminal amino acid sequence thereof was determined in the procedure described in Example 2. As a result, the amino acid sequence accorded with the N-terminal amino acid sequence (SEQ ID NO: 1) of STCE1.

(2) Evaluation of Fuzz-Removing Activity in Culture of STCE1 Transformant

Culture supernatants of two strains of *Trichoderma viride* transformants expressing STCE1, obtained in Example 16(1), and the parent strain (MC300-1) as a nontransformant were used. In accordance with the procedure described in Example 3, the blue cotton knit fabrics with fuzz were treated at pH 10 (5 mmol/L sodium carbonate buffer) and 40° C. for 1 hour with each culture supernatant, to calculate a protein concentration required to remove approximately 50% of the formed fuzz on the basis of a visual evaluation.

The protein concentration was determined using a Protein Assay Kit (BioRad Laboratories) and bovine serum albumin (as a standard). The result is shown in Table 9.

TABLE 9

| | Protein concentration required to remove 50% of fuzz from cotton fabric (mg/L) |
|---|---|
| *Trichoderma viride* MC300-1 (wild type) | Even when 330 mg/L was added, 50% of fuzz was not removed. |
| *Trichoderma viride* (STCE1N-pCB1 transformant) | 27 |
| *Trichoderma viride* (STCE1M-pCB1 transformant) | 28 |

INDUSTRIAL APPLICABILITY

The novel endoglucanases STCE of the present invention are useful in, for example, treating a cellulose-containing fabric, deinking waste paper, improving a water freeness of paper pulp, or improving a digestibility of animal feed.

Although the present invention has been described with reference to specific embodiments, various changes and modifications obvious to those skilled in the art are possible without departing from the scope of the appended claims.

BRIEF DESCRIPTION OF THE DRAWINGS

FIG. 1 is a part (the N-terminal side) of an alignment of the amino acid sequences of endoglucanase STCE1 [signal peptide (SEQ ID NO: 33) and mature protein (SEQ ID NO: 3)] of the present invention, known endoglucanase NCE4 [signal peptide (SEQ ID NO: 34) and mature protein (SEQ ID NO: 35)] belonging to family 45, and known endoglucanase NCE5 [signal peptide (SEQ ID NO: 36) and mature protein (SEQ ID NO: 37)] belonging to family 45.

FIG. 2 is the remaining part (the C-terminal side) of the alignment shown in FIG. 1.

Free Text in Sequence Listing

Features of "Artificial Sequence" are described in the numeric identifier <223> in the Sequence Listing. Each of the nucleotide sequences of SEQ ID NOS: 18-21 is primer STCE1-CN, primer STCE1-CC, primer STCE-HNBam, and primer STCE-HCBam. Each of the nucleotide sequences of SEQ ID NOS: 23-32 is primer NCE4-N-BamHI, primer NCE4-C-BamHI, primer STCE1-N-S9A4, primer STCE1-C-FokF, primer STCE1-N-FokR4, primer STCE1-C-BamF, primer STCE1-N-SmaI, primer STCE1-C-XhoI, primer STCE1-M-SphI, and primer STCE1-C-XhoI.

The invention claimed is:

1. An isolated protein having an endoglucanase activity, obtained from a microorganism belonging to genus *Staphylotrichum*, wherein said isolated protein is selected from the group consisting of:
   (a) a protein comprising the amino acid sequence of SEQ ID NO:3, and
   (b) a homologous protein comprising an amino acid sequence having at least an 95% identity with SEQ ID NO:3, and having an endoglucanase activity.

2. The isolated protein according to claim 1, having the amino acid sequence of SEQ ID NO: 1 at the N-terminus thereof.

3. The isolated protein according to claim 2, having an average molecular weight of 49 kD, determined by a sodium dodecyl sulfate-polyacrylamide gel electrophoresis.

4. The isolated protein according to claim 2, having an average molecular weight of 45 kD, determined by a sodium dodecyl sulfate-polyacrylamide gel electrophoresis.

5. The isolated protein according to claim 1, derived from *Staphylotrichum coccosporum*.

6. An isolated polynucleotide encoding the protein according to claim 1.

7. An isolated polynucleotide that encodes the isolated protein of claim 1, selected from the group consisting of:
   (i) a polynucleotide comprising the nucleotide sequence consisting of nucleotides 64-948 of SEQ ID NO : 2, and
   (ii) a polynucleotide hybridizing under stringent conditions to a polynucleotide consisting of the nucleotide sequence consisting of nucleotides 64-948 of SEQ ID NO: 2, and encoding a protein having an endoglucanase activity,
   wherein the stringent conditions comprise hybridization at 42° C. for 15 hours, washing with 0.4 or less ×SSC containing 0.4% SDS and 6 mol/L of urea at 42° C. for 20 minutes twice, and washing with 5×SSC at room temperature for 10 minutes twice.

8. An expression vector comprising the polynucleotide according to claim 6.

9. A host cell transformed with the expression vector according to claim 8.

10. The host cell according to claim 9, wherein the host is a yeast or a filamentous fungus.

11. The host cell according to claim 10, wherein the yeast is a microorganism belonging to genus *Saccharomyces, Hansenula,* or *Pichia*.

12. The host cell according to claim 10, wherein the filamentous fungus is a microorganism belonging to genus *Humicola, Trichoderma, Staphylotrichum, Aspergillus, Fusarium,* or *Acremonium*.

13. The host cell according to claim 12, the filamentous fungus is *Humicola insolens* or *Trichoderma viride*.

14. A process for producing the protein according to claim 1, comprising the steps of cultivating a host cell transformed with an expression vector selected from the group consisting of:
   an expression vector comprising a polynucleotide encoding the protein of (a) and,
   an expression vector comprising a polynucleotide encoding the homologous protein of (b), and collecting the protein from the host cell or a culture obtained by the cultivation.

15. An isolated protein produced by a process comprising:
cultivating a host cell transformed with an expression vector comprising a polynucleotide encoding the protein according to claim 1; and
collecting the protein from the host cell or a culture obtained by the cultivation.

16. A cellulase preparation comprising the protein according to claim 1.

17. A detergent composition comprising the protein according to claim 1.

18. A method of treating a cellulose-containing fabric, comprising the step of bringing the cellulose-containing fabric into contact with the protein according to claim 1.

19. A method of reducing fuzzing of a cellulose-containing fabric or reducing a rate of the formation of fuzz, comprising the step of bringing the cellulose-containing fabric into contact with the protein according to claim 1.

20. A method of reducing weight to improve the touch feel and appearance of a cellulose-containing fabric, comprising the step of bringing the cellulose-containing fabric into contact with the protein according to claim 1.

21. A method of color clarification of a colored cellulose-containing fabric, comprising the step of bringing the colored cellulose-containing fabric into contact with the protein according to claim 1.

22. A method of providing a localized color change to a colored cellulose-containing fabric, comprising the step of bringing the colored cellulose-containing fabric into contact with the protein according to claim 1.

23. A method of reducing stiffness of a cellulose-containing fabric or reducing a rate of the formation of stiffness, comprising the step of bringing the cellulose-containing fabric into contact with the protein according to claim 1.

24. The method according to claim 18, wherein the treatment of the fabric is carried out by soaking, washing, or rinsing the fabric.

25. A method of deinking waste paper, comprising the step of treating the waste paper with the protein according to claim 1.

26. A method of improving a water freeness of paper pulp, comprising the step of treating the paper pulp with the protein according to claim 1.

27. A method of improving a digestibility of animal feed, comprising the step of treating a cellulose-containing animal feed with the protein according to claim 1.

* * * * *

SEQUENCE LISTING

<160> NUMBER OF SEQ ID NOS: 37

<210> SEQ ID NO 1
<211> LENGTH: 25
<212> TYPE: PRT
<213> ORGANISM: Staphylotrichum coccosporum IFO 31817

<400> SEQUENCE: 1

Ala Asp Gly Lys Ser Thr Arg Tyr Trp Asp Cys Cys Lys Pro Ser Cys
1               5                   10                  15

Ser Trp Pro Gly Lys Ala Ser Val Asn
            20                  25

<210> SEQ ID NO 2
<211> LENGTH: 951
<212> TYPE: DNA
<213> ORGANISM: Staphylotrichum coccosporum IFO 31817
<220> FEATURE:
<221> NAME/KEY: sig_peptide
<222> LOCATION: (1)..(63)
<220> FEATURE:
<221> NAME/KEY: CDS
<222> LOCATION: (64)..(951)

<400> SEQUENCE: 2
atgcgttcct cccccgtcct ccgcacggcc ctggccgctg ccctccccct ggccgccctc        60 gct gcc gat ggc aag tcg acc cgc tac tgg gac tgt tgc aag ccg tcg       108
Ala Asp Gly Lys Ser Thr Arg Tyr Trp Asp Cys Cys Lys Pro Ser
    1               5                   10                  15 tgc tcg tgg ccc ggc aag gcc tcg gtg aac cag ccc gtc ttc gcc tgc       156
Cys Ser Trp Pro Gly Lys Ala Ser Val Asn Gln Pro Val Phe Ala Cys
                    20                  25                  30 agc gcc aac ttc cag cgc atc agc gac ccc aac gtc aag tcg ggc tgc       204
Ser Ala Asn Phe Gln Arg Ile Ser Asp Pro Asn Val Lys Ser Gly Cys
                35                  40                  45 gac ggc ggc tcc gcc tac gcc tgc gcc gac cag acc ccg tgg gcc gtc       252
Asp Gly Gly Ser Ala Tyr Ala Cys Ala Asp Gln Thr Pro Trp Ala Val
        50                  55                  60 aac gac aac ttc tcg tac ggc ttc gcc gcc acg tcc atc tcg ggc ggc       300
Asn Asp Asn Phe Ser Tyr Gly Phe Ala Ala Thr Ser Ile Ser Gly Gly
65                  70                  75 aac gag gcc tcg tgg tgc tgt ggc tgc tac gag ctg acc ttc acc tcg       348
Asn Glu Ala Ser Trp Cys Cys Gly Cys Tyr Glu Leu Thr Phe Thr Ser
80                  85                  90                  95 ggc ccc gtc gct ggc aag acc atg gtt gtc cag tcc acc tcg acc ggc       396
Gly Pro Val Ala Gly Lys Thr Met Val Val Gln Ser Thr Ser Thr Gly
                    100                 105                 110 ggc gac ctc ggc acc aac cac ttc gac ctg gcc atg ccc ggt ggt ggt       444
Gly Asp Leu Gly Thr Asn His Phe Asp Leu Ala Met Pro Gly Gly Gly
                115                 120                 125 gtc ggc atc ttc gac ggc tgc tcg ccc cag ttc ggc ggc ctc gcc ggc       492
Val Gly Ile Phe Asp Gly Cys Ser Pro Gln Phe Gly Gly Leu Ala Gly
        130                 135                 140 gac cgc tac ggc ggc gtc tcg tcg cgc agc cag tgc gac tcg ttc ccc       540
Asp Arg Tyr Gly Gly Val Ser Ser Arg Ser Gln Cys Asp Ser Phe Pro
    145                 150                 155 gcc gcc ctc aag ccc ggc tgc tac tgg cgc ttc gac tgg ttc aag aac       588
Ala Ala Leu Lys Pro Gly Cys Tyr Trp Arg Phe Asp Trp Phe Lys Asn
160                 165                 170                 175 gcc gac aac ccg acc ttc acc ttc cgc cag gtc cag tgc ccg tcg gag       636

```
Ala Asp Asn Pro Thr Phe Thr Phe Arg Gln Val Gln Cys Pro Ser Glu
                180                 185                 190 ctc gtc gcc cgc acc ggc tgc cgc cgc aac gac gac ggc aac ttc ccc          684
Leu Val Ala Arg Thr Gly Cys Arg Arg Asn Asp Asp Gly Asn Phe Pro
        195                 200                 205 gtc ttc acc cct ccc tcg ggt cag tcc tcc tcg tct tcc tcc tcc              732
Val Phe Thr Pro Pro Ser Gly Gln Ser Ser Ser Ser Ser Ser Ser
        210                 215                 220 agc agc gcc aag ccc acc tcc acc tcc acc tcg acc acc tcc acc aag          780
Ser Ser Ala Lys Pro Thr Ser Thr Ser Thr Ser Thr Thr Ser Thr Lys
        225                 230                 235 gct acc tcc acc acc tcg acc gcc tcc agc cag acc tcg tcg tcc acc          828
Ala Thr Ser Thr Thr Ser Thr Ala Ser Ser Gln Thr Ser Ser Ser Thr
240                 245                 250                 255 ggc ggc ggc tgc gcc gcc cag cgc tgg gcg cag tgc ggc ggc atc ggg          876
Gly Gly Gly Cys Ala Ala Gln Arg Trp Ala Gln Cys Gly Gly Ile Gly
                260                 265                 270 ttc tcg ggc tgc acc acg tgc gtc agc ggc acc acc tgc aac aag cag          924
Phe Ser Gly Cys Thr Thr Cys Val Ser Gly Thr Thr Cys Asn Lys Gln
                275                 280                 285 aac gac tgg tac tcg cag tgc ctt taa                                      951
Asn Asp Trp Tyr Ser Gln Cys Leu
        290                 295

<210> SEQ ID NO 3
<211> LENGTH: 295
<212> TYPE: PRT
<213> ORGANISM: Staphylotrichum coccosporum IFO 31817

<400> SEQUENCE: 3

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Ala Gly Asp
        130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
```

-continued

```
              210                 215                 220
Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
                275                 280                 285

Asp Trp Tyr Ser Gln Cys Leu
    290                 295

<210> SEQ ID NO 4
<211> LENGTH: 8
<212> TYPE: PRT
<213> ORGANISM: Staphylotrichum coccosporum IFO 31817

<400> SEQUENCE: 4

Pro Ser Cys Ser Trp Pro Gly Lys
1               5

<210> SEQ ID NO 5
<211> LENGTH: 9
<212> TYPE: PRT
<213> ORGANISM: Staphylotrichum coccosporum IFO 31817

<400> SEQUENCE: 5

Ser Thr Arg Tyr Trp Asp Cys Cys Lys
1               5

<210> SEQ ID NO 6
<211> LENGTH: 10
<212> TYPE: PRT
<213> ORGANISM: Staphylotrichum coccosporum IFO 31817

<400> SEQUENCE: 6

Asn Ala Asp Asn Pro Thr Phe Thr Phe Arg
1               5                   10

<210> SEQ ID NO 7
<211> LENGTH: 10
<212> TYPE: PRT
<213> ORGANISM: Staphylotrichum coccosporum IFO 31817

<400> SEQUENCE: 7

Ala Ser Val Asn Gln Pro Val Phe Ala Cys
1               5                   10

<210> SEQ ID NO 8
<211> LENGTH: 7
<212> TYPE: PRT
<213> ORGANISM: Staphylotrichum coccosporum IFO 31817

<400> SEQUENCE: 8

Pro Gly Cys Tyr Trp Arg Phe
1               5

<210> SEQ ID NO 9
<211> LENGTH: 7
<212> TYPE: PRT
<213> ORGANISM: Staphylotrichum coccosporum IFO 31817

<400> SEQUENCE: 9
```

```
Thr Met Val Val Gln Ser Thr
1               5

<210> SEQ ID NO 10
<211> LENGTH: 9
<212> TYPE: PRT
<213> ORGANISM: Staphylotrichum coccosporum IFO 31817

<400> SEQUENCE: 10

Gln Asn Asp Trp Tyr Ser Gln Cys Leu
1               5

<210> SEQ ID NO 11
<211> LENGTH: 8
<212> TYPE: PRT
<213> ORGANISM: Staphylotrichum coccosporum IFO 31817

<400> SEQUENCE: 11

Pro Ser Cys Ser Trp Pro Gly Lys
1               5

<210> SEQ ID NO 12
<211> LENGTH: 9
<212> TYPE: PRT
<213> ORGANISM: Staphylotrichum coccosporum IFO 31817

<400> SEQUENCE: 12

Ser Thr Arg Tyr Trp Asp Cys Cys Lys
1               5

<210> SEQ ID NO 13
<211> LENGTH: 10
<212> TYPE: PRT
<213> ORGANISM: Staphylotrichum coccosporum IFO 31817

<400> SEQUENCE: 13

Asn Ala Asp Asn Pro Thr Phe Thr Phe Arg
1               5                   10

<210> SEQ ID NO 14
<211> LENGTH: 16
<212> TYPE: PRT
<213> ORGANISM: Staphylotrichum coccosporum IFO 31817

<400> SEQUENCE: 14

Ala Ser Val Asn Gln Pro Val Phe Ala Cys Ser Ala Asn Phe Gln Arg
1               5                   10                  15

<210> SEQ ID NO 15
<211> LENGTH: 22
<212> TYPE: PRT
<213> ORGANISM: Staphylotrichum coccosporum IFO 31817

<400> SEQUENCE: 15

Ser Gly Cys Asp Gly Gly Ser Ala Tyr Ala Cys Ala Asp Gln Thr Pro
1               5                   10                  15

Trp Ala Val Asn Asp Asn
            20

<210> SEQ ID NO 16
<211> LENGTH: 11
<212> TYPE: PRT
<213> ORGANISM: Staphylotrichum coccosporum IFO 31817
```

```
<400> SEQUENCE: 16

Pro Gly Cys Tyr Trp Arg Phe Asp Trp Phe Lys
1               5                   10

<210> SEQ ID NO 17
<211> LENGTH: 16
<212> TYPE: PRT
<213> ORGANISM: Staphylotrichum coccosporum IFO 31817

<400> SEQUENCE: 17

Thr Met Val Val Gln Ser Thr Ser Thr Gly Gly Asp Leu Gly Thr Asn
1               5                   10                  15

<210> SEQ ID NO 18
<211> LENGTH: 26
<212> TYPE: DNA
<213> ORGANISM: Artificial Sequence
<220> FEATURE:
<223> OTHER INFORMATION: Chemically synthesized Primer STCE1-CN

<400> SEQUENCE: 18
gcggatccat gcgttcctcc cccgtc                                        26

<210> SEQ ID NO 19
<211> LENGTH: 28
<212> TYPE: DNA
<213> ORGANISM: Artificial Sequence
<220> FEATURE:
<223> OTHER INFORMATION: Chemically synthesized Primer STCE1-CC

<400> SEQUENCE: 19
gcggatcctt aaaggcactg cgagtacc                                      28

<210> SEQ ID NO 20
<211> LENGTH: 39
<212> TYPE: DNA
<213> ORGANISM: Artificial Sequence
<220> FEATURE:
<223> OTHER INFORMATION: Chemically synthesized Primer STCE-HNBam

<400> SEQUENCE: 20
gggggatcct gggacaagat gcgttcctcc cccgtcctc                          39

<210> SEQ ID NO 21
<211> LENGTH: 35
<212> TYPE: DNA
<213> ORGANISM: Artificial Sequence
<220> FEATURE:
<223> OTHER INFORMATION: Chemically synthesized Primer STCE-HCBam

<400> SEQUENCE: 21
gggggatccg ctcaaaggca ctgcgagtac cagtc                              35

<210> SEQ ID NO 22
<211> LENGTH: 1037
<212> TYPE: DNA
<213> ORGANISM: Staphylotrichum coccosporum IFO 31817
<220> FEATURE:
<221> NAME/KEY: sig_peptide
<222> LOCATION: (1)..(63)
<220> FEATURE:
<221> NAME/KEY: exon
<222> LOCATION: (64)..(333)
<220> FEATURE:
<221> NAME/KEY: exon
<222> LOCATION: (420)..(1037)
<220> FEATURE:
```

-continued

```
<221> NAME/KEY: Intron
<222> LOCATION: (334)..(419)

<400> SEQUENCE: 22
atgcgttcct ccccgtcct ccgcacggcc ctggccgctg ccctccccct ggccgccctc      60 gct gcc gat ggc aag tcg acc cgc tac tgg gac tgt tgc aag ccg tcg     108
Ala Asp Gly Lys Ser Thr Arg Tyr Trp Asp Cys Cys Lys Pro Ser
 1               5                  10                  15 tgc tcg tgg ccc ggc aag gcc tcg gtg aac cag ccc gtc ttc gcc tgc     156
Cys Ser Trp Pro Gly Lys Ala Ser Val Asn Gln Pro Val Phe Ala Cys
             20                  25                  30 agc gcc aac ttc cag cgc atc agc gac ccc aac gtc aag tcg ggc tgc     204
Ser Ala Asn Phe Gln Arg Ile Ser Asp Pro Asn Val Lys Ser Gly Cys
         35                  40                  45 gac ggc ggc tcc gcc tac gcc tgc gcc gac cag acc ccg tgg gcc gtc     252
Asp Gly Gly Ser Ala Tyr Ala Cys Ala Asp Gln Thr Pro Trp Ala Val
     50                  55                  60 aac gac aac ttc tcg tac ggc ttc gcc gcc acg tcc atc tcg ggc ggc     300
Asn Asp Asn Phe Ser Tyr Gly Phe Ala Ala Thr Ser Ile Ser Gly Gly
 65                  70                  75 aac gag gcc tcg tgg tgc tgt ggc tgc tac gag tgagtgcttc ccccccccc    353
Asn Glu Ala Ser Trp Cys Cys Gly Cys Tyr Glu
 80                  85                  90 ccccccccac cccggttcg gtccttgcc gtgccttctt catactaacc gcctacccc      413 tccagg ctg acc ttc acc tcg ggc ccc gtc gct ggc aag acc atg gtt     461
       Leu Thr Phe Thr Ser Gly Pro Val Ala Gly Lys Thr Met Val
                        95                 100 gtc cag tcc acc tcg acc ggc ggc gac ctc ggc acc aac cac ttc gac     509
Val Gln Ser Thr Ser Thr Gly Gly Asp Leu Gly Thr Asn His Phe Asp
105                 110                 115                 120 ctg gcc atg ccc ggt ggt ggt gtc ggc atc ttc gac ggc tgc tcg ccc     557
Leu Ala Met Pro Gly Gly Gly Val Gly Ile Phe Asp Gly Cys Ser Pro
                125                 130                 135 cag ttc ggc ggc ctc gcc ggc gac cgc tac ggc ggc gtc tcg tcg cgc     605
Gln Phe Gly Gly Leu Ala Gly Asp Arg Tyr Gly Gly Val Ser Ser Arg
            140                 145                 150 agc cag tgc gac tcg ttc ccc gcc gcc ctc aag ccc ggc tgc tac tgg     653
Ser Gln Cys Asp Ser Phe Pro Ala Ala Leu Lys Pro Gly Cys Tyr Trp
        155                 160                 165 cgc ttc gac tgg ttc aag aac gcc gac aac ccg acc ttc acc ttc cgc     701
Arg Phe Asp Trp Phe Lys Asn Ala Asp Asn Pro Thr Phe Thr Phe Arg
    170                 175                 180 cag gtc cag tgc ccg tcg gag ctc gtc gcc cgc acc ggc tgc cgc cgc     749
Gln Val Gln Cys Pro Ser Glu Leu Val Ala Arg Thr Gly Cys Arg Arg
185                 190                 195                 200 aac gac gac ggc aac ttc ccc gtc ttc acc cct ccc tcg ggc ggt cag     797
Asn Asp Asp Gly Asn Phe Pro Val Phe Thr Pro Pro Ser Gly Gly Gln
                205                 210                 215 tcc tcc tcg tct tcc tcc tcc agc agc gcc aag ccc acc tcc acc tcc     845
Ser Ser Ser Ser Ser Ser Ser Ser Ala Lys Pro Thr Ser Thr Ser
            220                 225                 230 acc tcg acc acc tcc acc aag gct acc tcc acc acc tcg acc gcc tcc     893
Thr Ser Thr Thr Ser Thr Lys Ala Thr Ser Thr Thr Ser Thr Ala Ser
        235                 240                 245 agc cag acc tcg tcg tcc acc ggc ggc tgc gcc gcc cag cgc tgg         941
Ser Gln Thr Ser Ser Ser Thr Gly Gly Cys Ala Ala Gln Arg Trp
    250                 255                 260 gcg cag tgc ggc ggc atc ggg ttc tcg ggc tgc acc acg tgc gtc agc     989
Ala Gln Cys Gly Gly Ile Gly Phe Ser Gly Cys Thr Thr Cys Val Ser
```

```
                265                 270                 275                 280
ggc acc acc tgc aac aag cag aac gac tgg tac tcg cag tgc ctt tga      1037
Gly Thr Thr Cys Asn Lys Gln Asn Asp Trp Tyr Ser Gln Cys Leu
                285                 290                 295
```

<210> SEQ ID NO 23
<211> LENGTH: 39
<212> TYPE: DNA
<213> ORGANISM: Artificial Sequence
<220> FEATURE:
<223> OTHER INFORMATION: Chemically synthesized Primer NCE4-N-BamHI

<400> SEQUENCE: 23
ggggatcctg ggacaagatg cgttcctccc ctctcctcc                           39

<210> SEQ ID NO 24
<211> LENGTH: 37
<212> TYPE: DNA
<213> ORGANISM: Artificial Sequence
<220> FEATURE:
<223> OTHER INFORMATION: Chemically synthesized Primer NCE4-C-BamHI

<400> SEQUENCE: 24
ggggatcctg cgtttacagg cactgatggt accagtc                             37

<210> SEQ ID NO 25
<211> LENGTH: 34
<212> TYPE: DNA
<213> ORGANISM: Artificial Sequence
<220> FEATURE:
<223> OTHER INFORMATION: Chemically synthesized Primer STCE1-N-S9A4

<400> SEQUENCE: 25
gggatcctgc gtttaaaggc actgcgagta ccag                                34

<210> SEQ ID NO 26
<211> LENGTH: 24
<212> TYPE: DNA
<213> ORGANISM: Artificial Sequence
<220> FEATURE:
<223> OTHER INFORMATION: Chemically synthesized Primer STCE1-C-FokF

<400> SEQUENCE: 26
gggatgcaag ccgtcgtgct cgtg                                           24

<210> SEQ ID NO 27
<211> LENGTH: 23
<212> TYPE: DNA
<213> ORGANISM: Artificial Sequence
<220> FEATURE:
<223> OTHER INFORMATION: Chemically synthesized Primer STCE1-N-FokR4

<400> SEQUENCE: 27
gggatgggcc cagccgcacg aag                                            23

<210> SEQ ID NO 28
<211> LENGTH: 20
<212> TYPE: DNA
<213> ORGANISM: Artificial Sequence
<220> FEATURE:
<223> OTHER INFORMATION: Chemically synthesized Primer STCE1-C-BamF

<400> SEQUENCE: 28
gggatcctgg gacaagatgc                                                20

```
<210> SEQ ID NO 29
<211> LENGTH: 35
<212> TYPE: DNA
<213> ORGANISM: Artificial Sequence
<220> FEATURE:
<223> OTHER INFORMATION: Chemically synthesized Primer STCE1-N-SmaI

<400> SEQUENCE: 29
cagcccgggg cgcatcatgc gttcctcccc tctcc                              35

<210> SEQ ID NO 30
<211> LENGTH: 33
<212> TYPE: DNA
<213> ORGANISM: Artificial Sequence
<220> FEATURE:
<223> OTHER INFORMATION: Chemically synthesized Primer STCE1-C-XhoI

<400> SEQUENCE: 30
gcctcgagta ccttaaaggc actgcgagta cca                                33

<210> SEQ ID NO 31
<211> LENGTH: 26
<212> TYPE: DNA
<213> ORGANISM: Artificial Sequence
<220> FEATURE:
<223> OTHER INFORMATION: Chemically synthesized Primer STCE1-M-SphI

<400> SEQUENCE: 31
ccgcatgcgc tgatggcaag tccacc                                        26

<210> SEQ ID NO 32
<211> LENGTH: 33
<212> TYPE: DNA
<213> ORGANISM: Artificial Sequence
<220> FEATURE:
<223> OTHER INFORMATION: Chemically synthesized Primer STCE1-C-XhoI

<400> SEQUENCE: 32
gcctcgagta ccttaaaggc actgcgagta cca                                33

<210> SEQ ID NO 33
<211> LENGTH: 21
<212> TYPE: PRT
<213> ORGANISM: Staphylotrichum coccosporum IFO 31817

<400> SEQUENCE: 33

Met Arg Ser Ser Pro Val Leu Arg Thr Ala Leu Ala Ala Ala Leu Pro
1               5                   10                  15

Leu Ala Ala Leu Ala
            20

<210> SEQ ID NO 34
<211> LENGTH: 20
<212> TYPE: PRT
<213> ORGANISM: Humicola insolens

<400> SEQUENCE: 34

Met Arg Ser Ser Pro Leu Leu Arg Ser Ala Val Val Ala Ala Leu Pro
1               5                   10                  15

Val Leu Ala Leu
            20

<210> SEQ ID NO 35
<211> LENGTH: 286
<212> TYPE: PRT
```

<213> ORGANISM: Humicola insolens

<400> SEQUENCE: 35

Ala Ala Asp Gly Lys Ser Thr Arg Tyr Trp Asp Cys Cys Lys Pro Ser
1               5                   10                  15

Cys Gly Trp Ala Lys Lys Ala Pro Val Asn Gln Pro Val Phe Ser Cys
            20                  25                  30

Asn Ala Asn Phe Gln Arg Leu Thr Asp Phe Asp Ala Lys Ser Gly Cys
        35                  40                  45

Glu Pro Gly Gly Val Ala Tyr Ser Cys Ala Asp Gln Thr Pro Trp Ala
    50                  55                  60

Val Asn Asp Asp Phe Ala Phe Gly Phe Ala Ala Thr Ser Ile Ala Gly
65                  70                  75                  80

Ser Asn Glu Ala Gly Trp Cys Cys Ala Cys Tyr Glu Leu Thr Phe Thr
                85                  90                  95

Ser Gly Pro Val Ala Gly Lys Lys Met Val Val Gln Ser Thr Ser Thr
            100                 105                 110

Gly Gly Asp Leu Gly Ser Asn His Phe Asp Leu Asn Ile Pro Gly Gly
        115                 120                 125

Gly Val Gly Ile Phe Asp Gly Cys Thr Pro Gln Phe Gly Gly Leu Pro
    130                 135                 140

Gly Gln Arg Tyr Gly Gly Ile Ser Ser Arg Asn Glu Cys Asp Arg Phe
145                 150                 155                 160

Pro Asp Ala Leu Lys Pro Gly Cys Tyr Trp Arg Phe Asp Trp Phe Lys
                165                 170                 175

Asn Ala Asp Asn Pro Ser Phe Ser Phe Arg Gln Val Gln Cys Pro Ala
            180                 185                 190

Glu Leu Val Ala Arg Thr Gly Cys Arg Arg Asn Asp Asp Gly Asn Phe
        195                 200                 205

Pro Ala Val Gln Ile Pro Ser Ser Ser Thr Ser Ser Pro Val Gly Gln
    210                 215                 220

Pro Thr Ser Thr Ser Thr Ser Thr Ser Thr Ser Thr Ser Ser Pro Pro
225                 230                 235                 240

Val Gln Pro Thr Thr Pro Ser Gly Cys Thr Ala Glu Arg Trp Ala Cys
                245                 250                 255

Gln Cys Gly Gly Asn Gly Trp Ser Gly Cys Thr Thr Cys Val Ala Gly
            260                 265                 270

Ser Thr Cys Thr Lys Ile Asn Asp Trp Tyr His Gln Cys Leu
        275                 280                 285

<210> SEQ ID NO 36
<211> LENGTH: 17
<212> TYPE: PRT
<213> ORGANISM: Humicola insolens

<400> SEQUENCE: 36

Met Gln Leu Pro Leu Thr Thr Leu Leu Thr Leu Leu Pro Ala Leu Ala
1               5                   10                  15

Ala

<210> SEQ ID NO 37
<211> LENGTH: 206
<212> TYPE: PRT
<213> ORGANISM: Humicola insolens

<400> SEQUENCE: 37

-continued

```
Ala Gln Ser Gly Ser Gly Arg Thr Thr Arg Tyr Trp Asp Cys Cys Lys
1               5                   10                  15

Pro Ser Cys Ala Trp Pro Gly Lys Gly Pro Ala Pro Val Arg Thr Cys
            20                  25                  30

Asp Arg Trp Asp Asn Pro Leu Phe Asp Gly Gly Asn Thr Arg Ser Gly
        35                  40                  45

Cys Asp Ala Gly Gly Gly Ala Tyr Met Cys Ser Asp Gln Ser Pro Trp
        50                  55                  60

Ala Val Ser Asp Asp Leu Ala Tyr Gly Trp Ala Ala Val Asn Ile Ala
65                  70                  75                  80

Gly Ser Asn Glu Arg Gln Trp Cys Cys Ala Cys Tyr Glu Leu Thr Phe
                85                  90                  95

Thr Ser Gly Pro Val Ala Gly Lys Arg Met Ile Val Gln Ala Ser Asn
                100                 105                 110

Thr Gly Gly Asp Leu Gly Asn Asn His Phe Asp Ile Ala Met Pro Gly
            115                 120                 125

Gly Gly Val Gly Ile Phe Asn Ala Cys Thr Asp Gln Tyr Gly Ala Pro
        130                 135                 140

Pro Asn Gly Trp Gly Gln Arg Tyr Gly Gly Ile Ser Gln Arg His Glu
145                 150                 155                 160

Cys Asp Ala Phe Pro Glu Lys Leu Lys Pro Gly Cys Tyr Trp Arg Phe
                165                 170                 175

Asp Trp Phe Leu Asn Ala Asp Asn Pro Ser Val Asn Trp Arg Gln Val
            180                 185                 190

Ser Cys Pro Ala Glu Ile Val Ala Lys Ser Gly Cys Ser Arg
            195                 200                 205
```